US011847931B2

(12) United States Patent
Lariviere et al.

(10) Patent No.: US 11,847,931 B2
(45) Date of Patent: Dec. 19, 2023

(54) ELECTRONICALLY ADJUSTABLE JOINT, AND ASSOCIATED SYSTEMS AND METHODS

(71) Applicant: Applied Minds, LLC, Burbank, CA (US)

(72) Inventors: Donald G Lariviere, Hollywood, CA (US); David Foor, Altadena, CA (US); Andrew McGraw, Newbury Park, CA (US); Michael Keesling, Agoura Hills, CA (US)

(73) Assignee: Applied Minds, LLC, Burbank, CA (US)

( * ) Notice: Subject to any disclaimer, the term of this patent is extended or adjusted under 35 U.S.C. 154(b) by 95 days.

(21) Appl. No.: 17/158,766

(22) Filed: Jan. 26, 2021

(65) Prior Publication Data
US 2021/0150934 A1 May 20, 2021

Related U.S. Application Data

(62) Division of application No. 15/189,968, filed on Jun. 22, 2016, now Pat. No. 10,909,884.

(Continued)

(51) Int. Cl.
*G09B 23/28* (2006.01)
*G09B 5/00* (2006.01)
(Continued)

(52) U.S. Cl.
CPC ............ *G09B 23/28* (2013.01); *A61F 5/0125* (2013.01); *B25J 9/0006* (2013.01); *G06F 3/011* (2013.01);
(Continued)

(58) Field of Classification Search
CPC .......... A61F 2005/0146; A61F 5/0125; G09B 19/00; G09B 9/00; G09B 5/00;
(Continued)

(56) References Cited

U.S. PATENT DOCUMENTS

| 5,167,229 A | 12/1992 | Peckham et al. |
| 2007/0282228 A1* | 12/2007 | Einav ............... A63B 21/00181 600/300 |

(Continued)

*Primary Examiner* — Timothy A Musselman
(74) *Attorney, Agent, or Firm* — Perkins Coie LLP; Michael A. Glenn

(57) ABSTRACT

Disclosed is an electronically adjustable joint, and associated systems and methods. A joint position of a multiple-axis joint, e.g., a 3-axis joint, can be tracked, as the joint moves through two or more dimensions. In an illustrative embodiment, the joint can provide a mechanical equivalent of a physical joint, e.g., a shoulder, elbow, hip, or knee, which can accommodate motion in rotational angle and/or tilt angle. In some embodiments, the joint includes electronically adjustable friction. An illustrative application provides electronically adjustable joints for an aging simulation suit, wherein one or more joints can be controllably stiffened in selective ranges, such that a wearer of the suit can experience the effects of aging, arthritis and/or other ailments. In an illustrative embodiment, a sensor can use four discrete 2-axis magnetometers to calculate the position of the magnet on the arm of the joint, to continuously sense and track the angle of the joint. In some embodiments, the system includes a mechanism, e.g., a servo, which can controllably tighten a socket around a ball joint, wherein the system can controllably adjust friction on the joint.

16 Claims, 24 Drawing Sheets

Related U.S. Application Data

(60) Provisional application No. 62/182,933, filed on Jun. 22, 2015.

(51) Int. Cl.
*A61F 5/01* (2006.01)
*G09B 9/00* (2006.01)
*G09B 19/00* (2006.01)
*G06F 3/01* (2006.01)
*B25J 9/00* (2006.01)

(52) U.S. Cl.
CPC ............... *G06F 3/014* (2013.01); *G09B 5/00* (2013.01); *G09B 9/00* (2013.01); *G09B 19/00* (2013.01); *A61F 2005/0146* (2013.01)

(58) Field of Classification Search
CPC ......... G09B 23/28; G06F 3/011; G06F 3/014; B25J 9/0006
See application file for complete search history.

(56) References Cited

U.S. PATENT DOCUMENTS

| | | |
|---|---|---|
| 2012/0010749 A1 | 1/2012 | van der Merwe et al. |
| 2015/0351995 A1 | 12/2015 | Zoss et al. |

\* cited by examiner

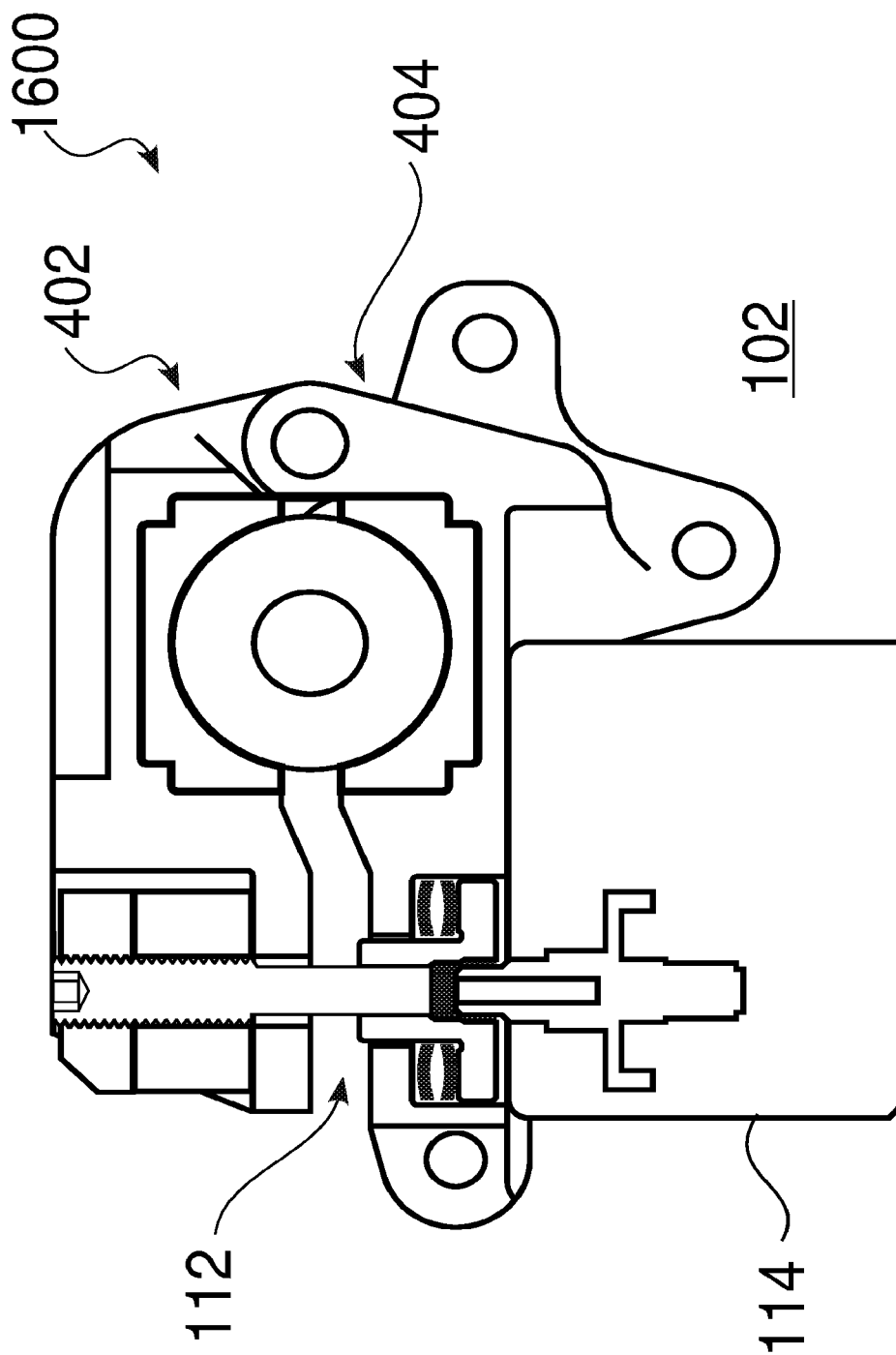

ELECTRONICALLY ADJUSTABLE JOINT, AND ASSOCIATED SYSTEMS AND METHODS

CROSS REFERENCE TO RELATED APPLICATIONS

This Application is a Divisional of and claims priority to U.S. patent application Ser. No. 15/189,968, filed 22 Jun. 2016, which was issued as U.S. Pat. No. 10,909,884 on 2 Feb. 2021, which claims priority to U.S. Provisional Application No. 62/182,933, filed 22 Jun. 2015, which is incorporated herein in its entirety by this reference thereto.

FIELD OF THE INVENTION

At least one embodiment of the present invention pertains to an electronically adjustable joint. Some embodiments pertain to methods for implementing a 3-axis joint with precise measurement of position and electronically controllable friction.

BACKGROUND

A number of suits have been created to demonstrate the effects of aging for younger wearers, typically by mechanically stiffening joints of the suit alongside the wearer's joints. Adjusting the level of friction requires a time-consuming manual adjustment to each joint, and it is not remotely adjustable during movement. Additionally, the friction setting is the same throughout the motion range; however, aging adults typically have varying ability of movement at different points in the range. For example, many older people find it difficult to lift their arms above their head.

If a joint is able to vary friction at various points in the motion range, it becomes important to be able to measure where the joint is in order to apply the appropriate setting. However, some joints, such as the shoulder, move in both rotation and tilt directions.

BRIEF DESCRIPTION OF THE DRAWINGS

One or more embodiments of the present invention are illustrated by way of example and not limitation in the figures of the accompanying drawings, in which like references indicate similar elements.

FIG. 25 is partial cutaway side view of an illustrative electronically adjustable joint.

DETAILED DESCRIPTION

References in this description to "an embodiment", "one embodiment", or the like, mean that the particular feature, function, structure or characteristic being described is included in at least one embodiment of the present invention. Occurrences of such phrases in this specification do not necessarily all refer to the same embodiment. On the other hand, the embodiments referred to also are not necessarily mutually exclusive.

Introduced here are improved methods, systems and devices to precisely track a joint position as it moves through two or more dimensions, such as a mechanical equivalent of a shoulder joint that accommodates motion in rotational and tilt angle.

In certain embodiments, joints are provided with electronically adjustable friction. One application of these goals is the use of the joint in an aging simulation suit, where joints are stiffened in selective ranges in order for wearers to experience the effects of aging, arthritis and other ailments.

To accomplish a goal of continuously sensing and tracking the angle of the joint, an illustrative sensor embodiment can use four discrete 2-axis magnetometers to calculate the position of a magnet that is located on the arm of the joint.

To accomplish the goal of electronically adjustable friction, a servo can be used to tighten a socket around a ball joint, thus increasing friction.

In one embodiment, an illustrative aging simulation suit comprises approximately 20 joints, with one servo located at each joint. Each servo can operate through a gear system, such as to controllably tighten a nut which stiffens the interface between two movable parts, e.g., to tighten a socket with respect to a ball. The servos electronically communicate with a control processor, through which an operator can send commands to stiffen or loosen each individual joint. Additionally, ranges of motion can be selected, such that a joint can be freely moved through a certain motion, then stiffen or lock up through another range of motion. To facilitate these adjustable ranges, the position of each joint can be precisely tracked.

Embodiments of the joints can use a ball-joint as a mostly unconstrained degree-of-freedom pivot. Stiffness to the joint is introduced by clamping down on the ball joint with a brake pad or other frictional material, which is milled to line the inside of the ball joint socket. The illustrative servos can tighten the socket around the ball joint, by rotating a jackscrew attached to a hinged clamp containing the two halves of the socket, thus increasing the force of the brake pad or other frictional material against the ball joint.

The disclosed devices, systems and methods have applicability beyond the above embodiment. In general, the illustrative disclosed devices, systems and methods cover precise tracking of a 2-axis joint (for example, rotation and tilt) and electronically adjustable friction adjustment.

Figure 1:
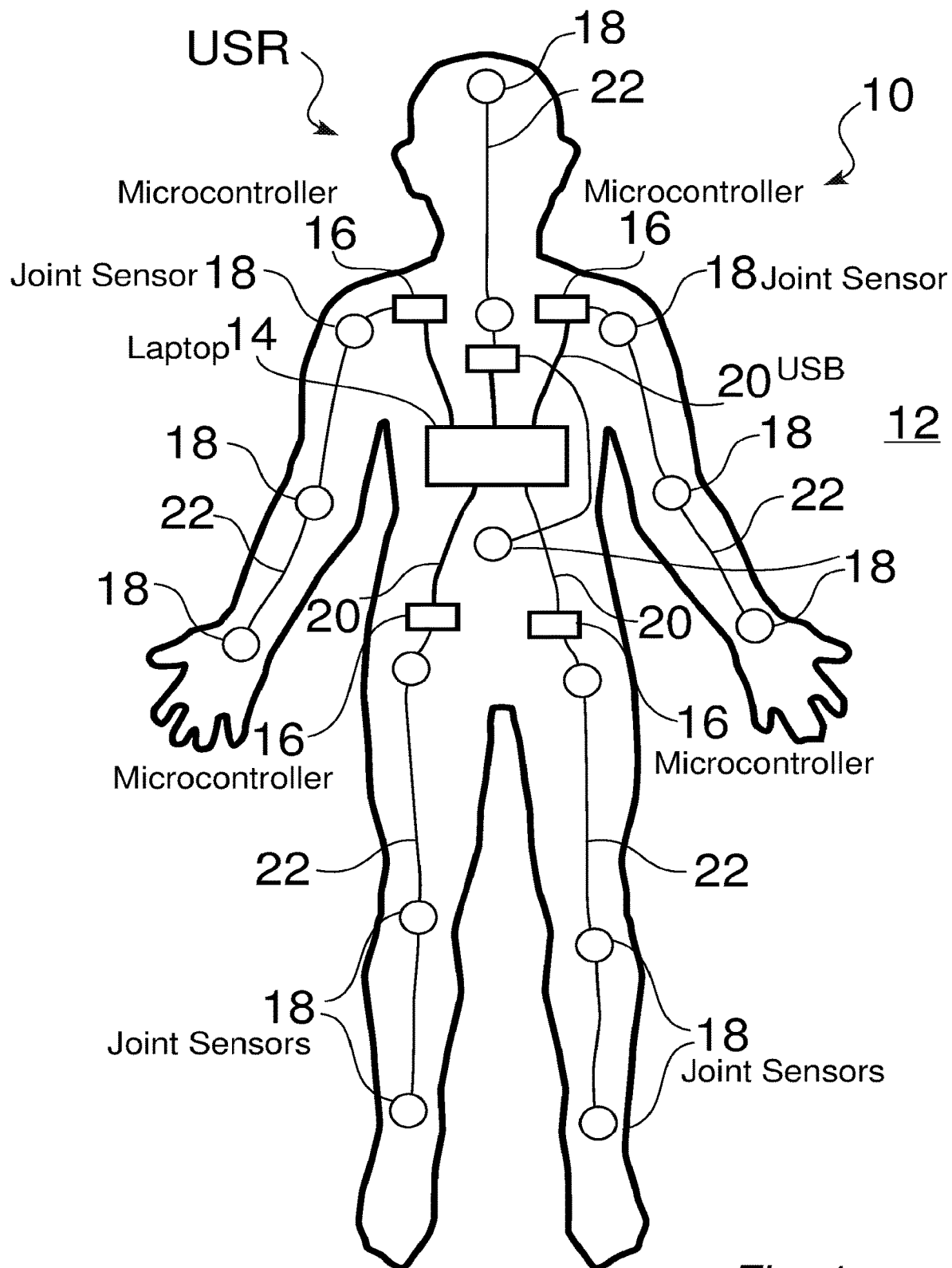
FIG. 1 is a schematic view of connectivity for an illustrative embodiment of an aging simulation suit having electronically adjustable joints.

FIG. 1 is a schematic view 10 showing connectivity for an illustrative embodiment of an aging simulation suit 62 (FIG. 2) that includes a plurality of electronically adjustable joints 102 (FIG. 3) and corresponding joint sensors 18. A plurality of joint sensors 18 are associated with corresponding joints 102, such as related to any of shoulders, elbows, wrists, hands, hips, knees, ankles, feet, torso, neck and head of a user USR. The joint sensors 18 can be connected 22 to a microcontroller 16, either directly, or through one or more other joint sensors 18. In some embodiments, the connection is provided by a bus 22, e.g., an IC2 bus. The microcontrollers 16 seen in FIG. 1 are in turn connected to a central processor 14, e.g., a laptop 14, such as by standard connections 20, e.g., USB connections 20. In some embodiments, a laptop 14 can be used for any of data acquisition for information received from one or more of the joint sensors, and/or for control signals sent through the microcontrollers 16, such as to controllably increase friction associated with one or more joints.

Figure 2:
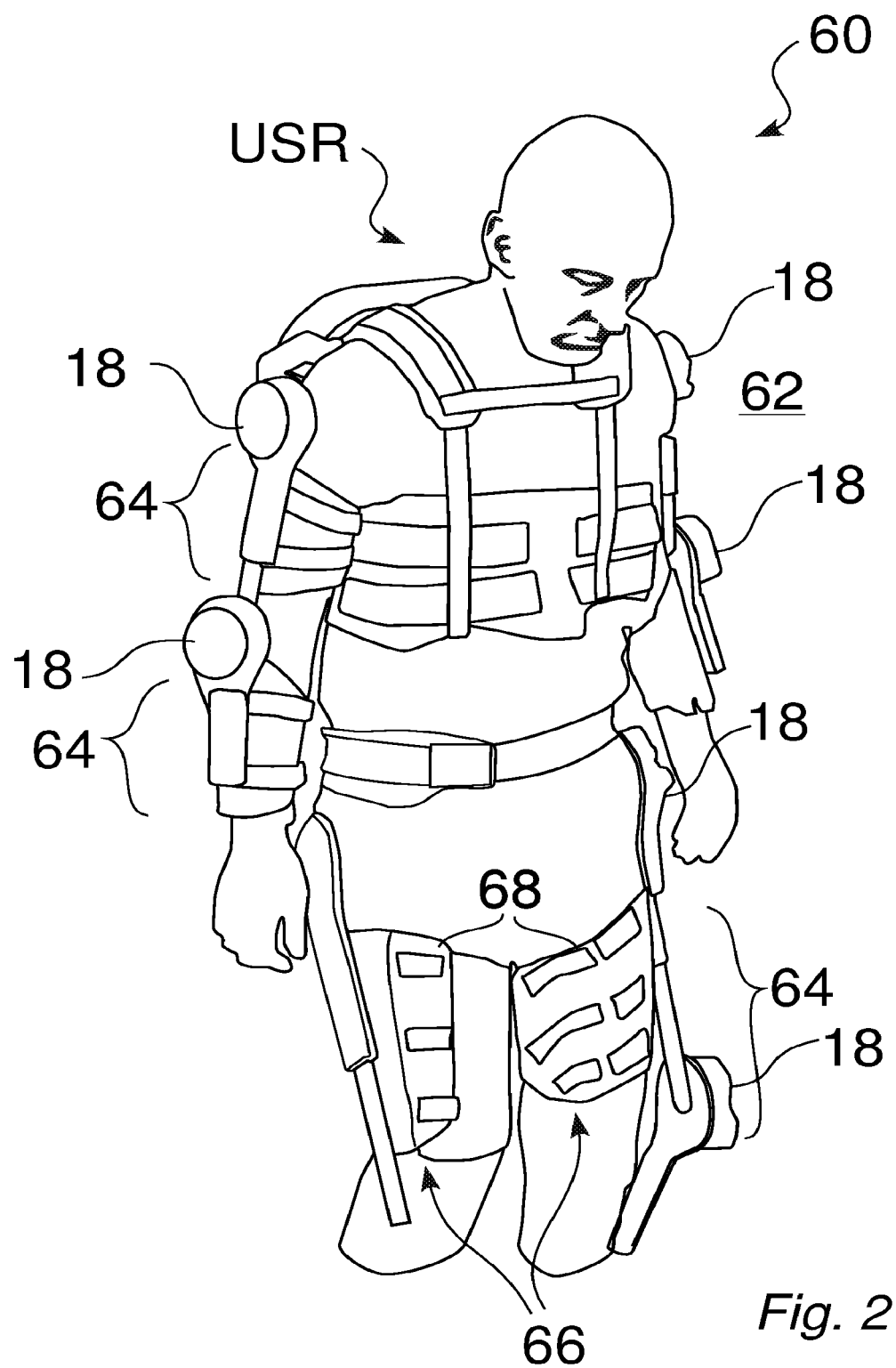
FIG. 2 shows a user wearing an illustrative aging simulation suit.

FIG. 2 is a perspective view 60 of a user USR wearing an illustrative aging simulation suit 62, which includes a mechanical structure 64 upon which each of the joint sensors 18 are located, and an attachment structure 66 through which the mechanical structure 64 can be attached to the user USR. The attachment structure 66, seen in FIG. 2, is attached 122 (FIG. 3) to the mechanical structure 64 and includes closures by which the suit 62 can be attached to the user USR. For example, the attachment structure 66 seen in FIG. 2 includes shoulder straps, a chest strap, a waist strap, arm straps, and leg straps 68. The mechanical structure 64 seen in FIG. 2 extends around the back of the user USR and includes a series of elements that pivotably connected through the electronically adjustable joints 102. For instance, the mechanical structure 64 seen in FIG. 2 includes joints 102 that correspond to the shoulders and elbows of the user USR, and joints 102 that correspond to the hips and knees of the user USR.

Figure 3:
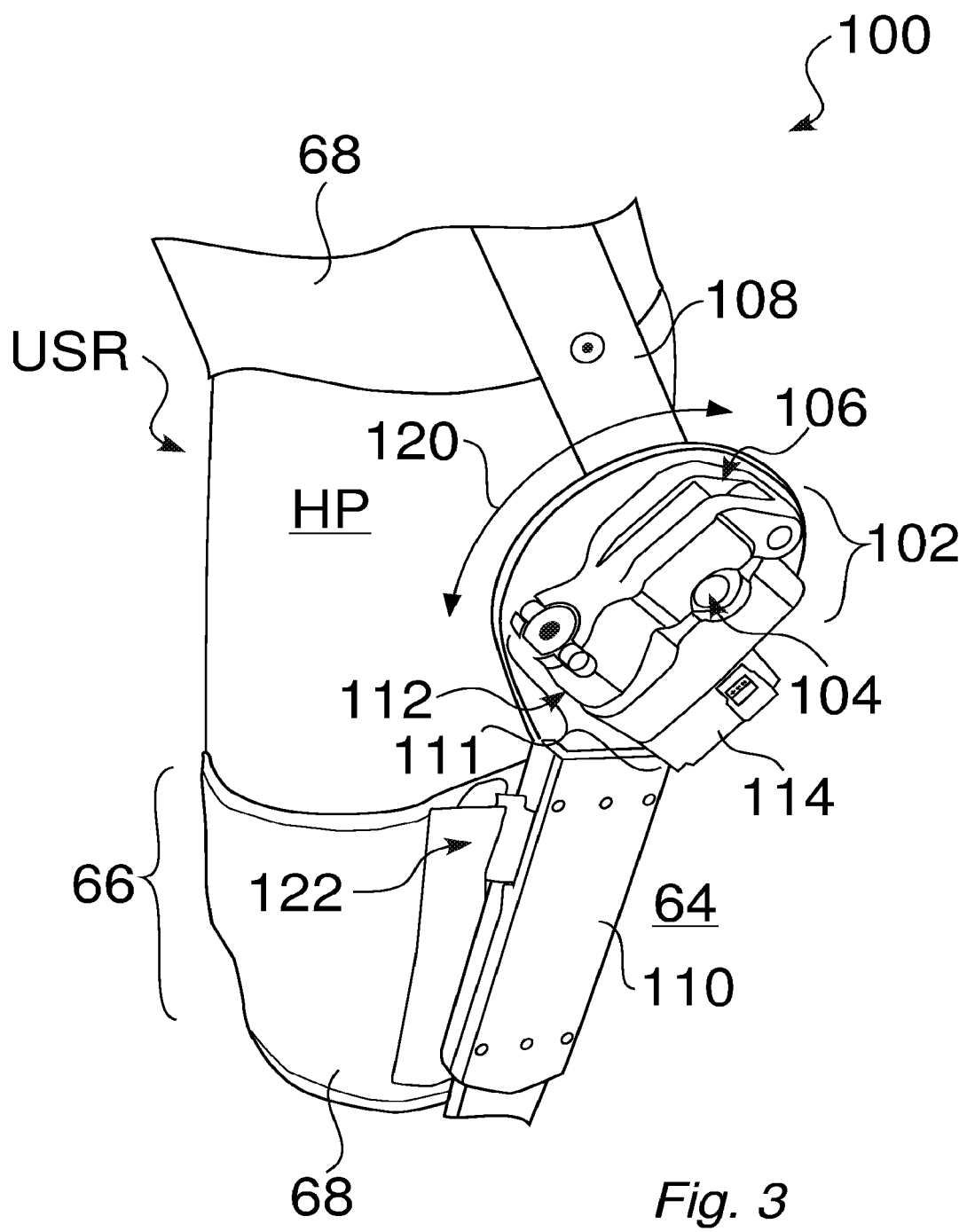
FIG. 3 is a close up view of an illustrative electronically adjustable joint being worn by a user.
Figure 4:
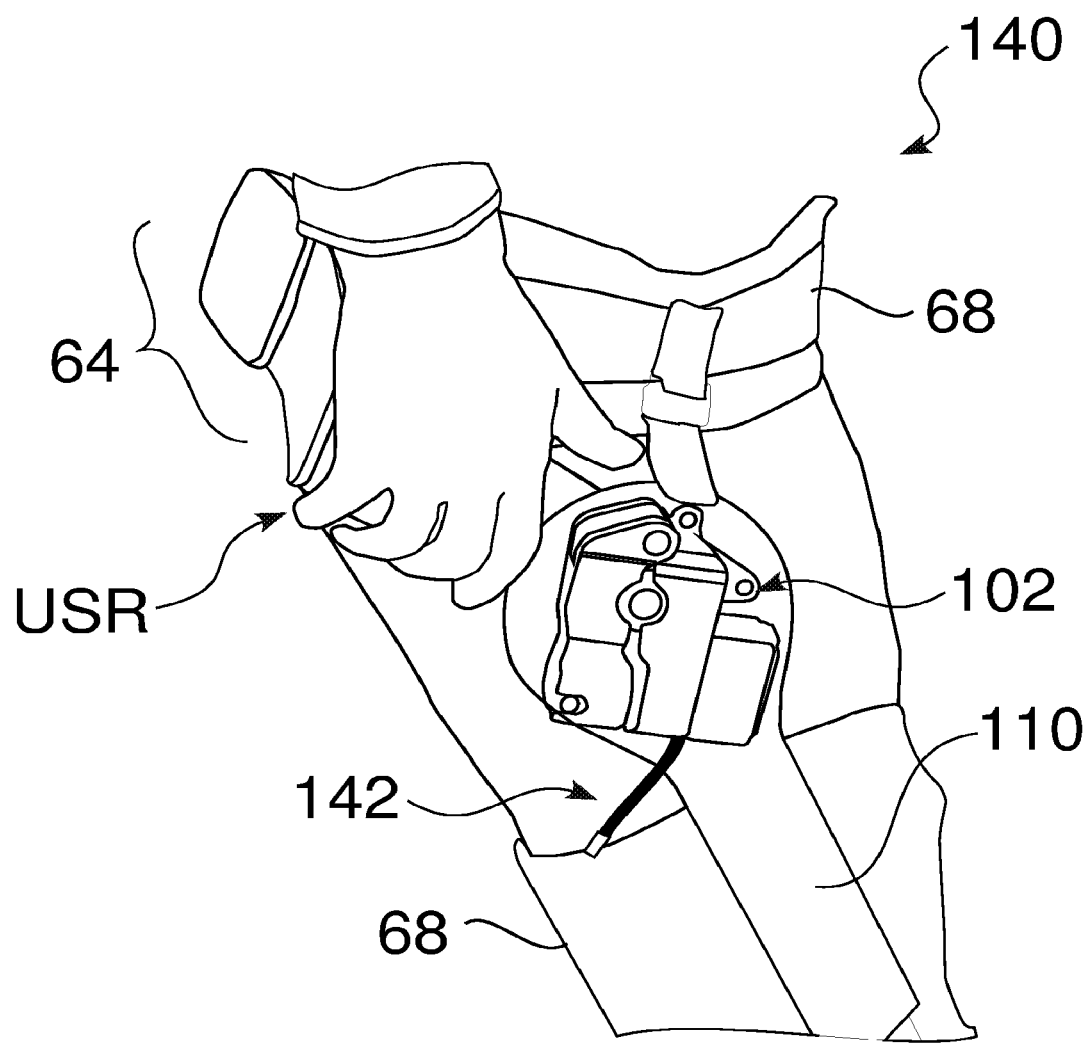
FIG. 4 is an alternate close up of an illustrative electronically adjustable joint being worn by a user.

FIG. 3 is a close up view 100 of an illustrative aging simulation suit 62 being worn by a user USR. FIG. 4 is an alternate close up view 140 of an illustrative aging simulation suit 62 being worn by a user USR. The illustrative aging simulation suit 62 seen in FIG. 3 and FIG. 4 show upper and lower leg straps 68 by which the aging simulation suit 62 is attached to the legs of a user USR. FIG. 3 and FIG. 4 also show details of the mechanical structure 64 of an illustrative embodiment of an aging simulation suit 62. For instance, an illustrative joint assembly 102 seen in FIG. 3 and FIG. 4 includes a pivot assembly 102 that is generally alignable with a hip HP of the user USR. The illustrative pivot assemblies 102 include a ball assembly 104 attached to a ball pivot arm 108, and a socket assembly 106 attached to a socket pivot arm 110. The illustrative socket assembly includes a socket defined 620 (FIG. 10) therein for confining the ball head 107 of the ball assembly 104.

The pivot assembly 102 allows rotational movement 120 of the ball head 602 (FIG. 11) within the socket 620 (FIG. 10), such as to correspond to movement of a hip HP of the user USR. The movement 120 can correspond to that of a 3-axis joint, i.e., for movement in two or more dimensions.

Figure 7:
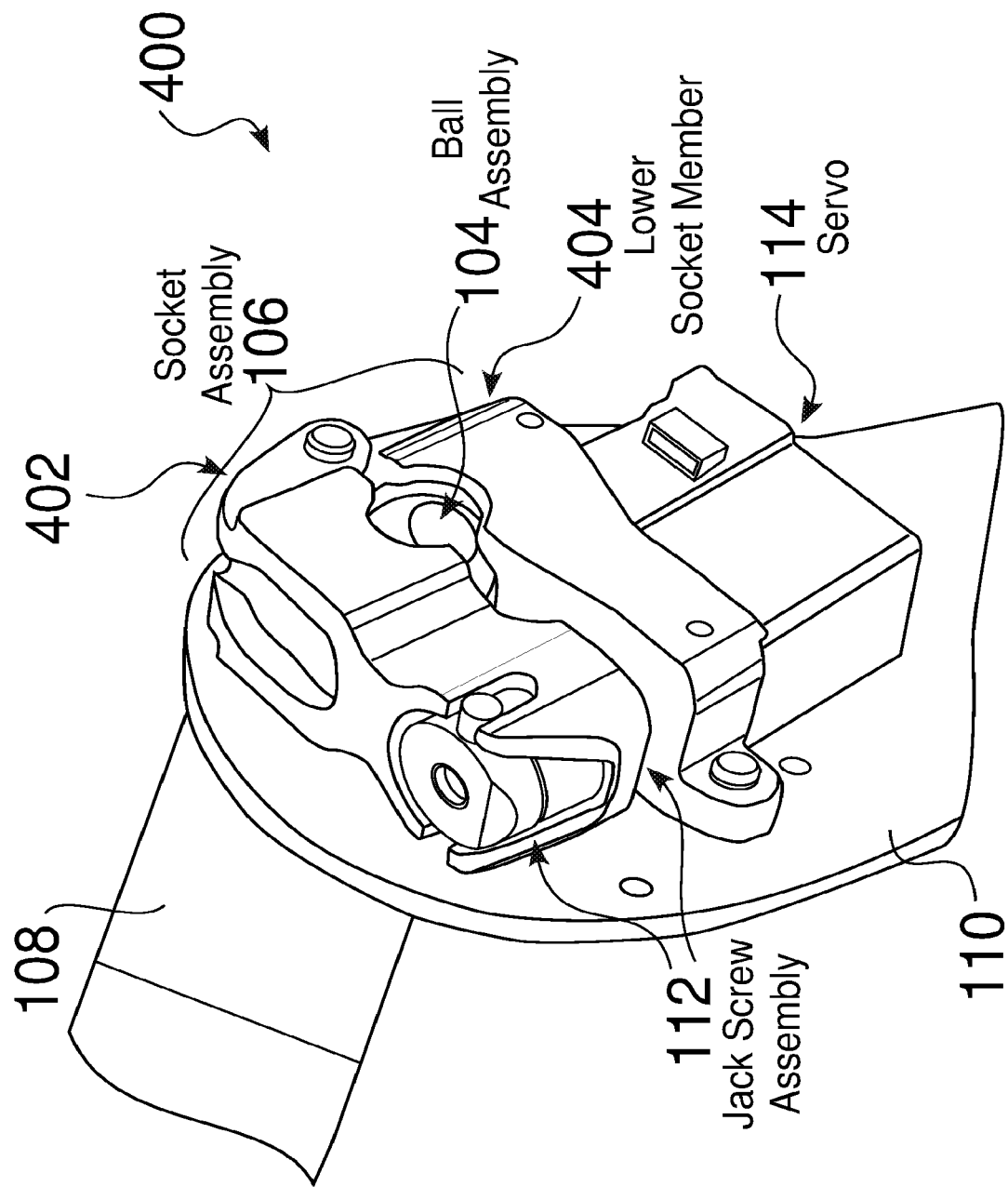
FIG. 7 is a close up view of an illustrative electronically adjustable joint.
Figure 19:
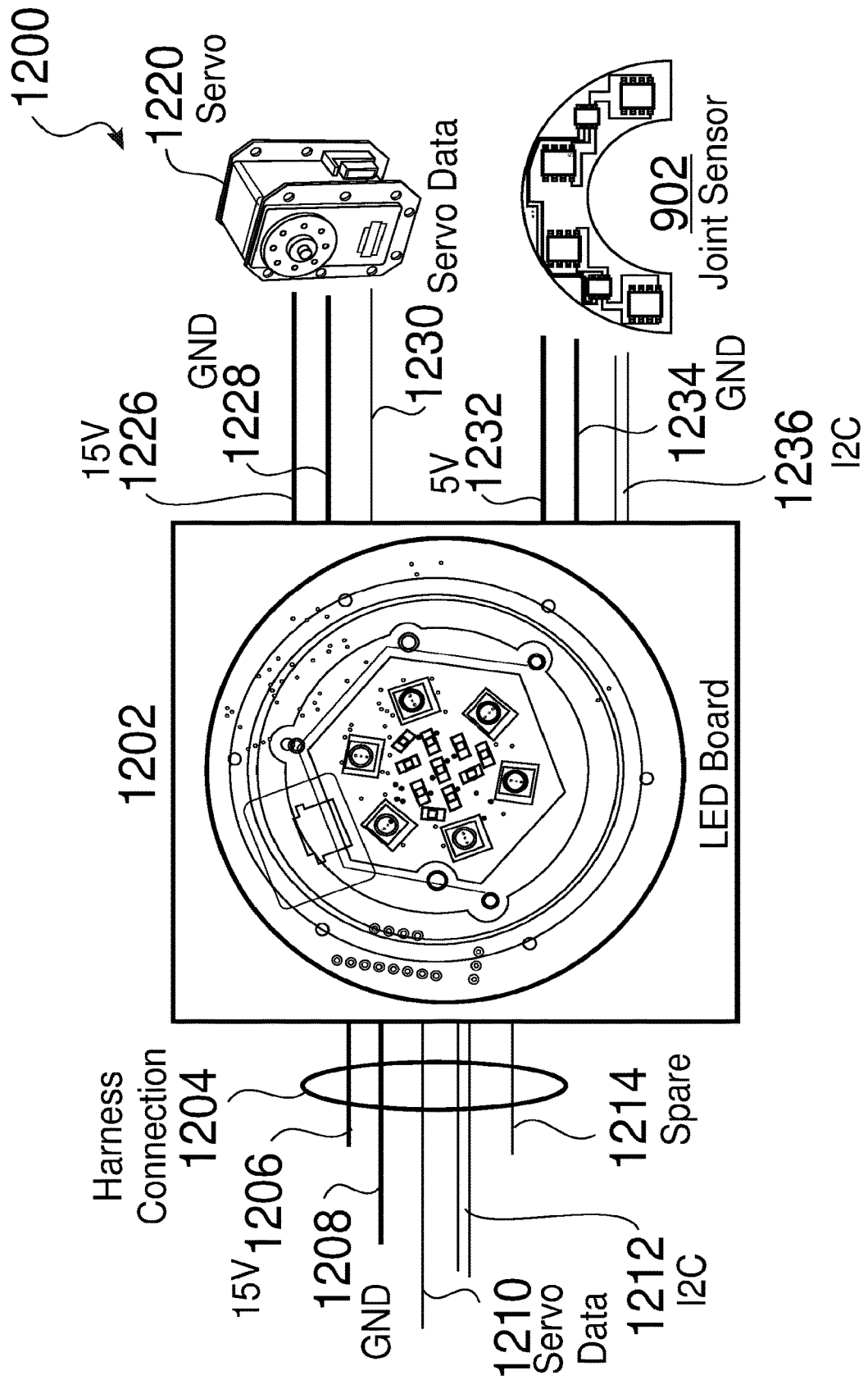
FIG. 19 shows an interconnection architecture for an illustrative electronically adjustable joint.

The illustrative socket assembly 106 seen in FIG. 3 and FIG. 4 includes a mechanism 111 by which to controllably adjust friction between the socket 620 and the ball 602, for movement in one or more directions of the rotation 120. For instance, the illustrative socket assembly 106 seen in FIG. 3 and FIG. 4 includes an adjustable jack screw assembly 112 that is controllably driven by a servo 114. The illustrative socket assembly 106 seen in FIG. 3 and FIG. 4 includes opposing socket assembly member 402 and 404, between which the jack screw assembly 112 extends. The illustrative servo 114 seen in FIG. 3 and FIG. 4 is mounted to a stationary lower socket member 404 (FIG. 7) and can controllably tighten or loosen the jack screw assembly 112 that is threadedly engaged to the opposing upper socket member 402 (FIG. 7). As seen in FIG. 4, an electrical connection 142 extends from the servo 114, such as to include power leads 1226, 1228 (FIG. 19) and a servo data lead 1230 (FIG. 19).

Command Interface

In one embodiment, the servo control 114 is designed as a command-line-based interface. In some embodiments, each joint servo 114 has a joint identifier and two modes of operation. In some embodiments, the interface can save the absolute position of all the servos 114. The torque required to achieve a given stiffness can be different from the torque required to maintain a given stiffness. However, a "baseline" absolute position can be recorded which allows for free motion at each joint 102, and then an offset from the baseline to achieve the desired stiffness setting which is related to the absolute position of the servo 114. Each of the servos 114 can include the ability to set a torque limit, such that the servo 114 can stop and report an error if and when the torque limit is reached.

In an illustrative embodiment, a processor 14, e.g., a laptop 14, can aggregate the data from five microcontrollers 16, each of which read three individual joints 102. In some embodiments, the interface 20 from the microcontrollers 16 to the laptop 14 is USB, and the interface 22 between each analog-digital converter (ADC) and the microcontroller 16 is the 12C protocol.

Servo Use Case

A high-level interface can incorporate sliders through which users can adjust stiffness of selected joints 102. A minimum stiffness can allow for free motion, while a maximum stiffness can solidly lock the joint.

A possible way to support this application can be the following:
 i) Select a joint 102 in the interface;
 ii) Drive the corresponding servo 114 and back the nut off until it just releases the joint 102;
 iii) Record this absolute position;
 iv) Drive the servo 114 until the nut causes the joint to be immovable; and
 v) Record this absolute position.

An interface slider can move the servo 114 from the position recorded in step iii to the position recorded in step v. The ability to lock a group of sliders such that they all adjust in the same way can be useful.

A more basic interface can include the ability to select a particular servo 114 and the ability to loosen or tighten it as needed.

Figure 5:
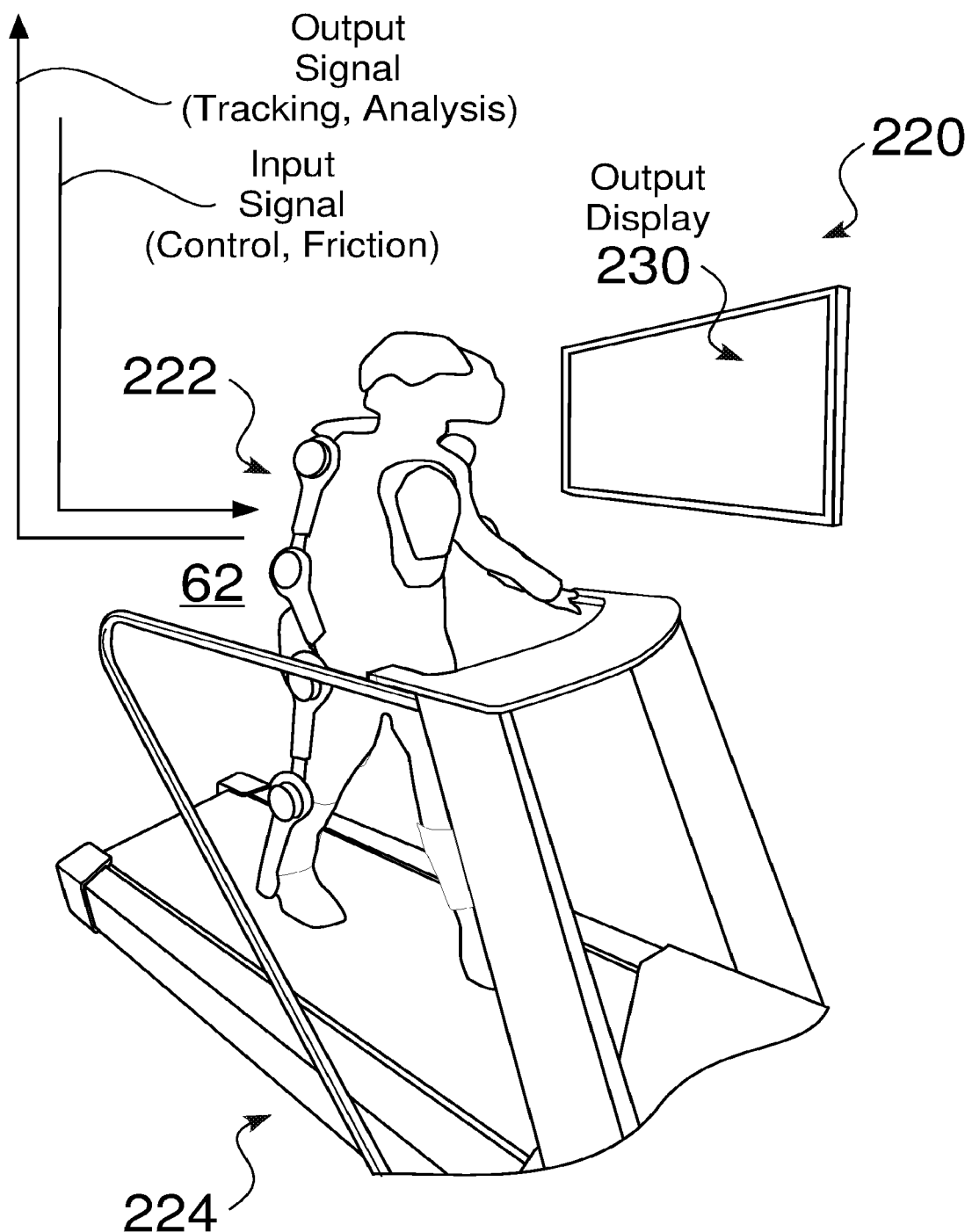
FIG. 5 shows an illustrative aging simulation suit as worn by a user during physical activity.

FIG. 5 is a view 220 that shows an illustrative aging simulation suit 62 as worn by a user USR during physical activity 222. For instance, a user USR wearing an aging simulation suit 62 can proceed with physical activity 222 within a physical test environment 224. The movement of one or more of the electronically adjustable joints 102 can be monitored, and in some embodiments, friction can be controllably applied for through one or more of the electronically adjustable joints 102 in one or more directions of the rotational motion 120.

Figure 6:
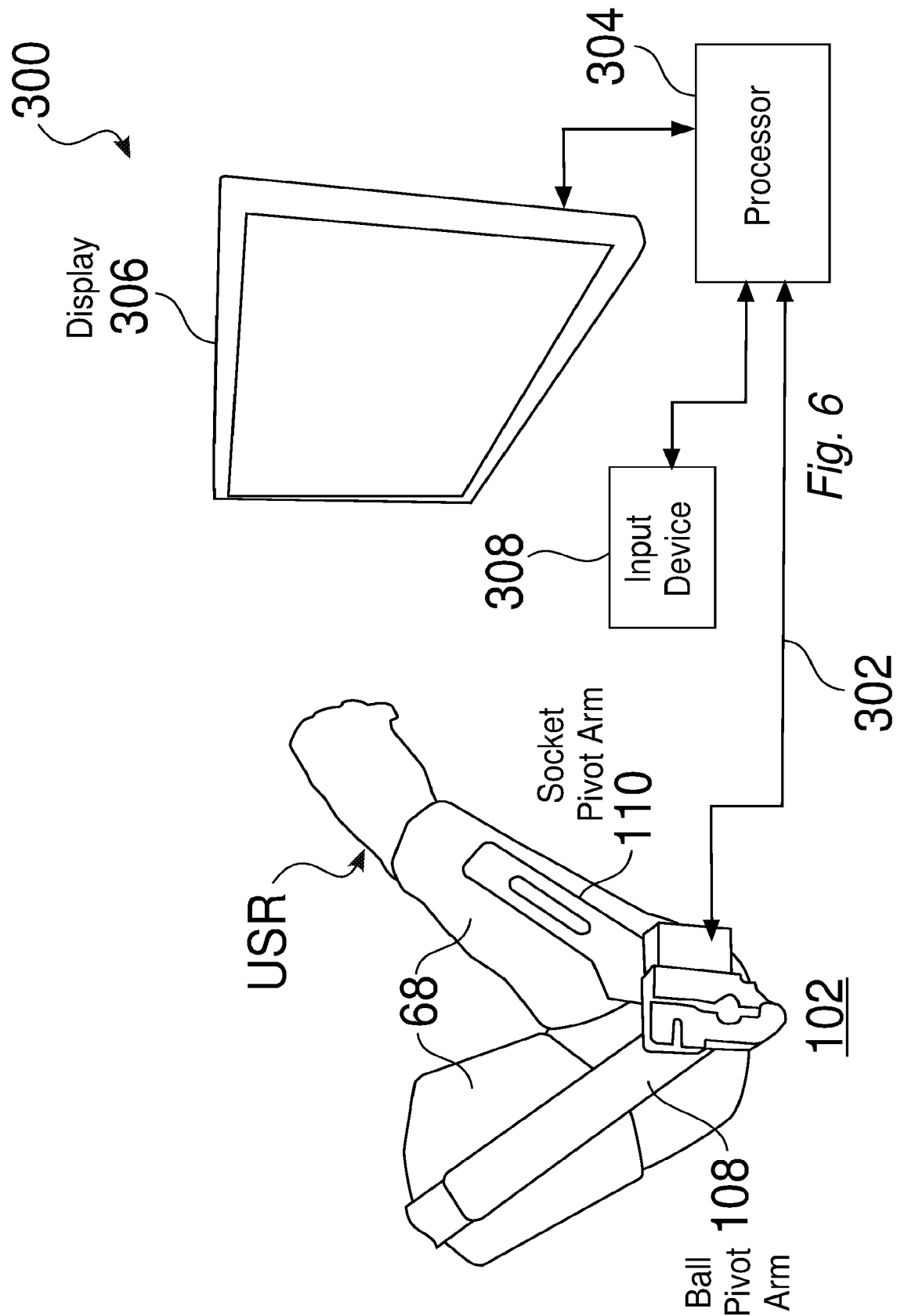
FIG. 6 shows an illustrative electronically adjustable joint being worn by a user and in communication with a processor.

FIG. 6 is a view 300 that shows an illustrative electronically adjustable joint structure 300 being worn by a user USR during physical activity 222. In contrast to an aging simulation suit 62, illustrative electronically adjustable joint structure 300 seen in FIG. 6 is configured for specific analysis and/or control of movement for a specific joint, e.g., an elbow. The movement can be tracked locally to the joint, such as with a joint sensor assembly 18, or can be tracked remotely, such as through localized sensors linked 302 to a processor 304. The illustrative test environment seen in FIG. 6 can also include input 308 to and output 306 from the processor 304, such as to set and/or alter test conditions, and/or to display joint movement, test parameters, and/or performance.

Figure 8:
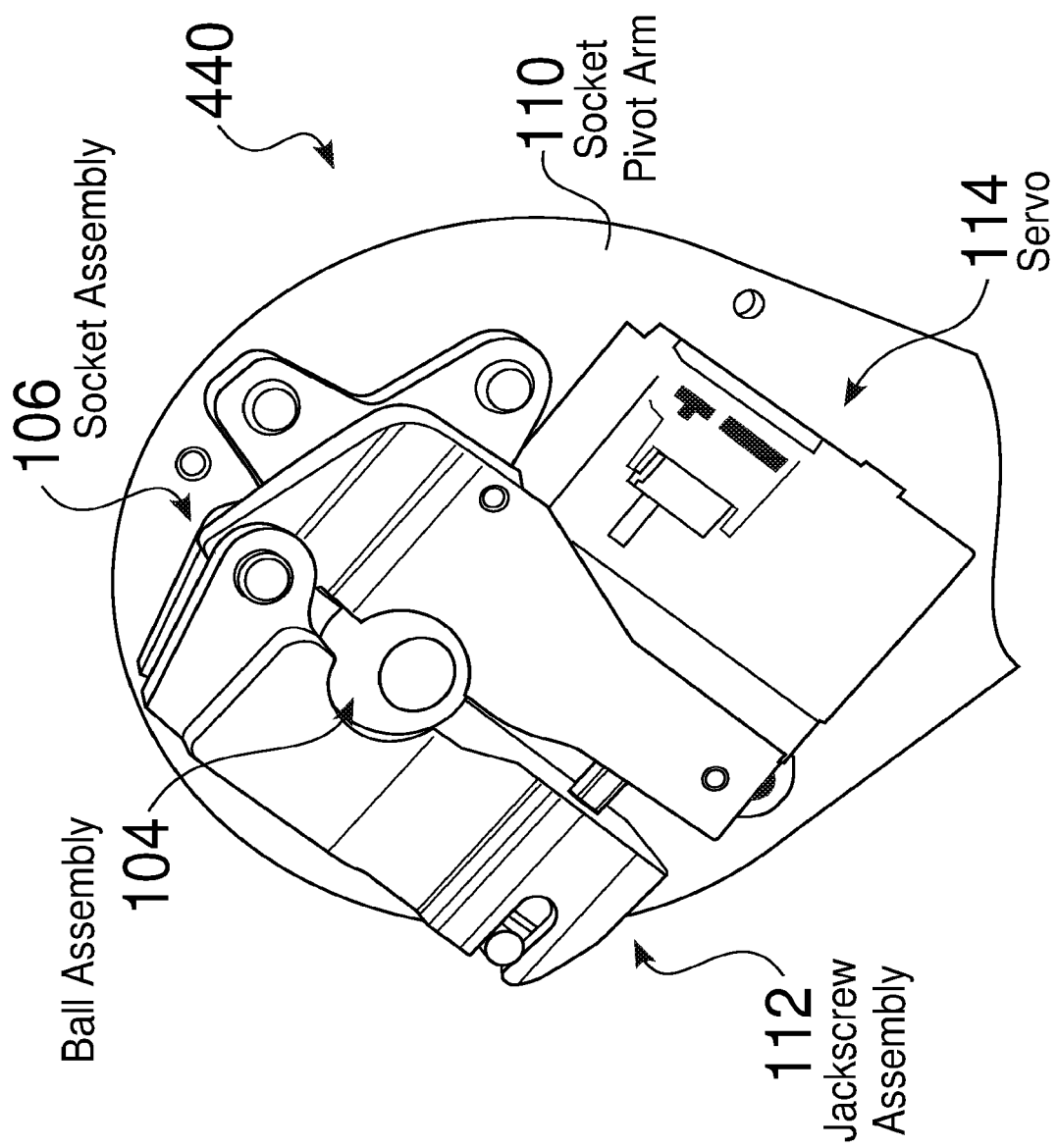
FIG. 8 shows an alternate detailed view of an illustrative electronically adjustable joint.
Figure 9:
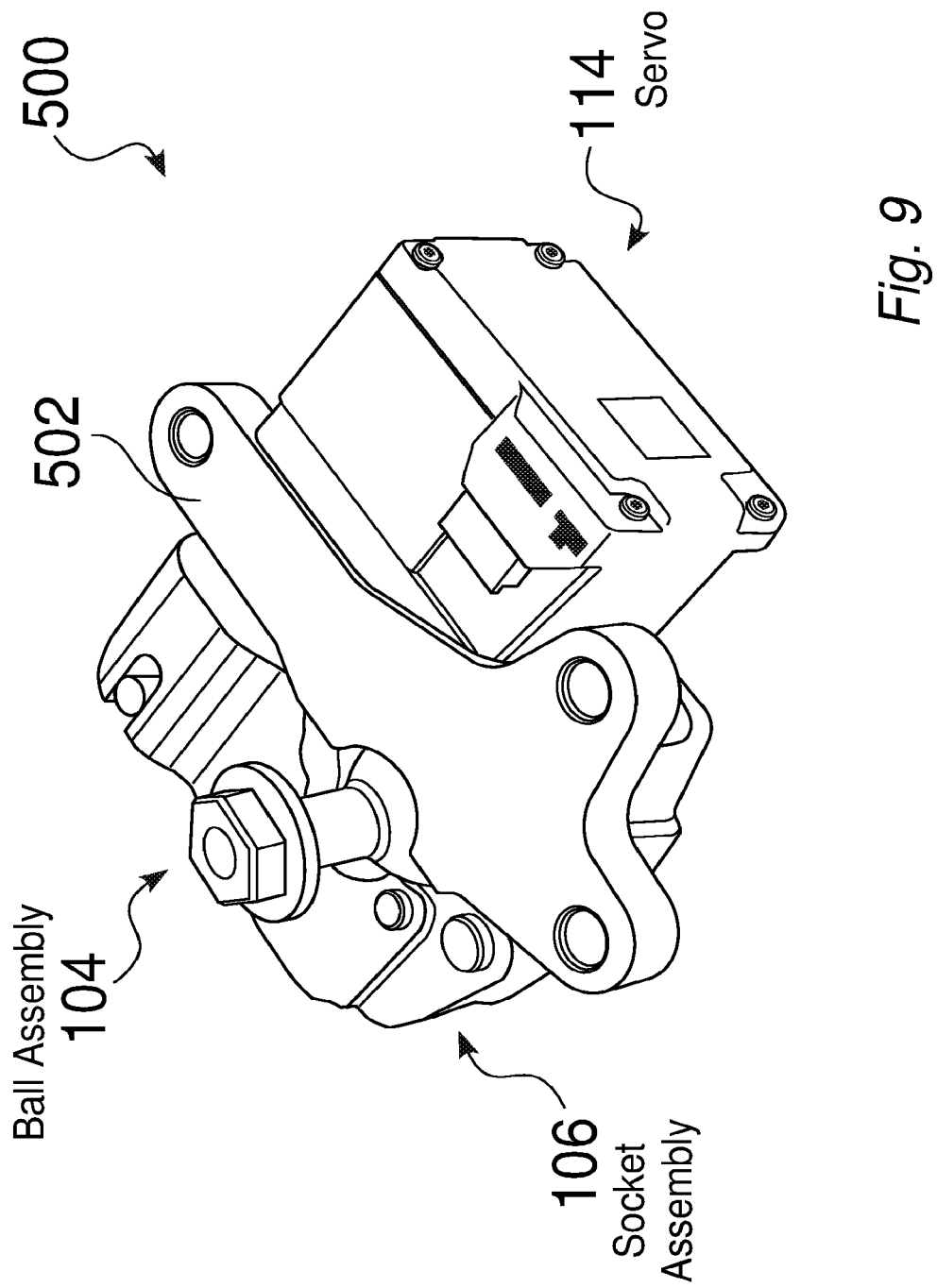
FIG. 9 is a detailed attachment side view of an illustrative electronically adjustable joint.

FIG. 7 is a close up view 400 of an illustrative electronically adjustable joint 102. FIG. 8 shows an alternate detailed view 440 of an illustrative electronically adjustable joint 102. FIG. 9 is a detailed pivot view 500 of an illustrative electronically adjustable joint 102, which shows the mounting plate 502 by which the socket assembly can be mounted to a socket pivot arm 110.

Figure 10:
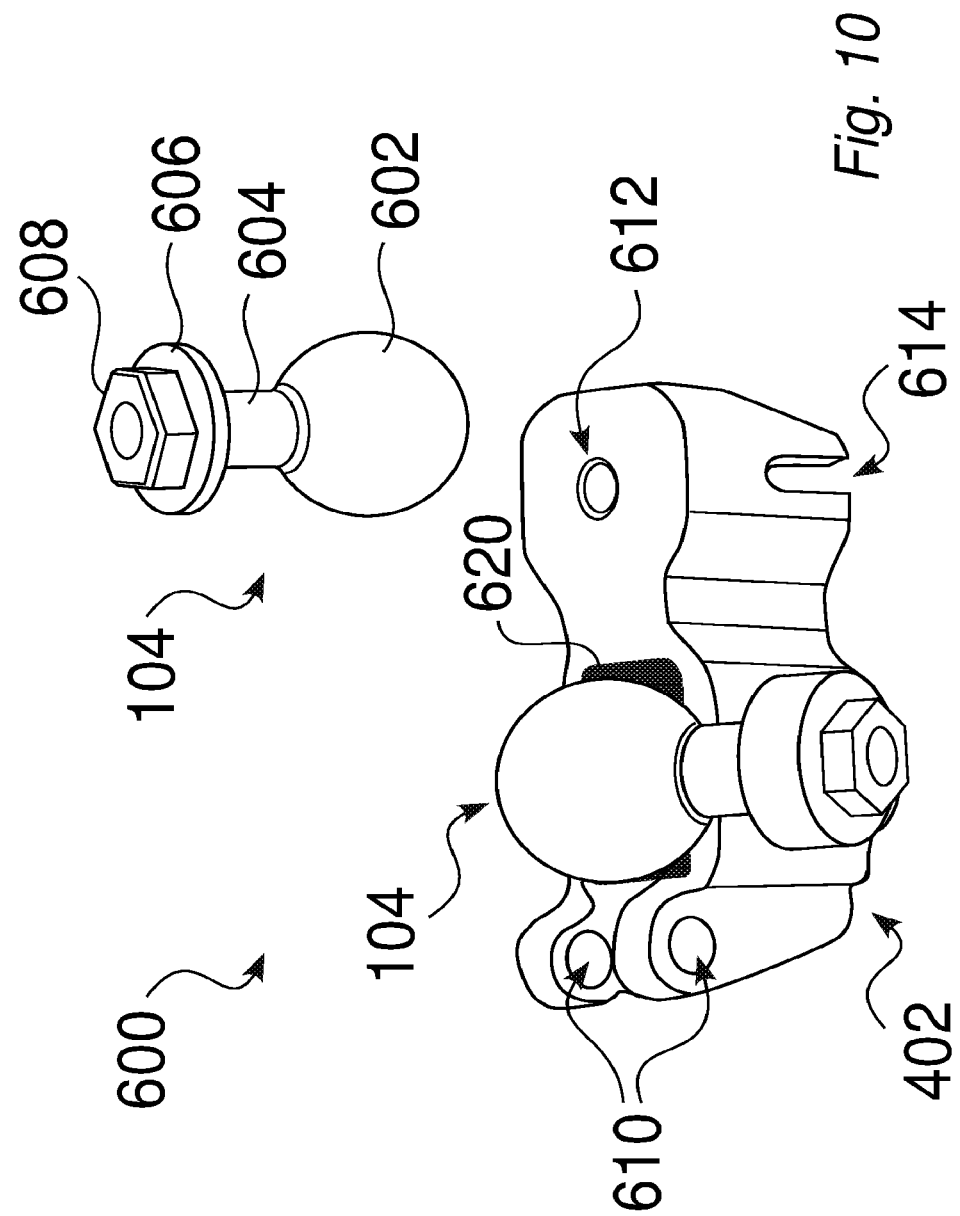
FIG. 10 is a perspective detailed view of ball joint assembly components for illustrative electronically adjustable joints.

FIG. 10 depicts a close up of ball and socket components 104 and 106 for illustrative electronically adjustable joints 102. For instance, the ball assemblies 104 seen in FIG. 10 include a ball 602 extending from a ball shaft 604, a ball landing 606, and ball assembly fastening mechanism 608. The upper socket member 402 seen in FIG. 10 includes pivot holes 610, a jack screw hole 612, and a jack screw retainer slot 614.

Figure 11:
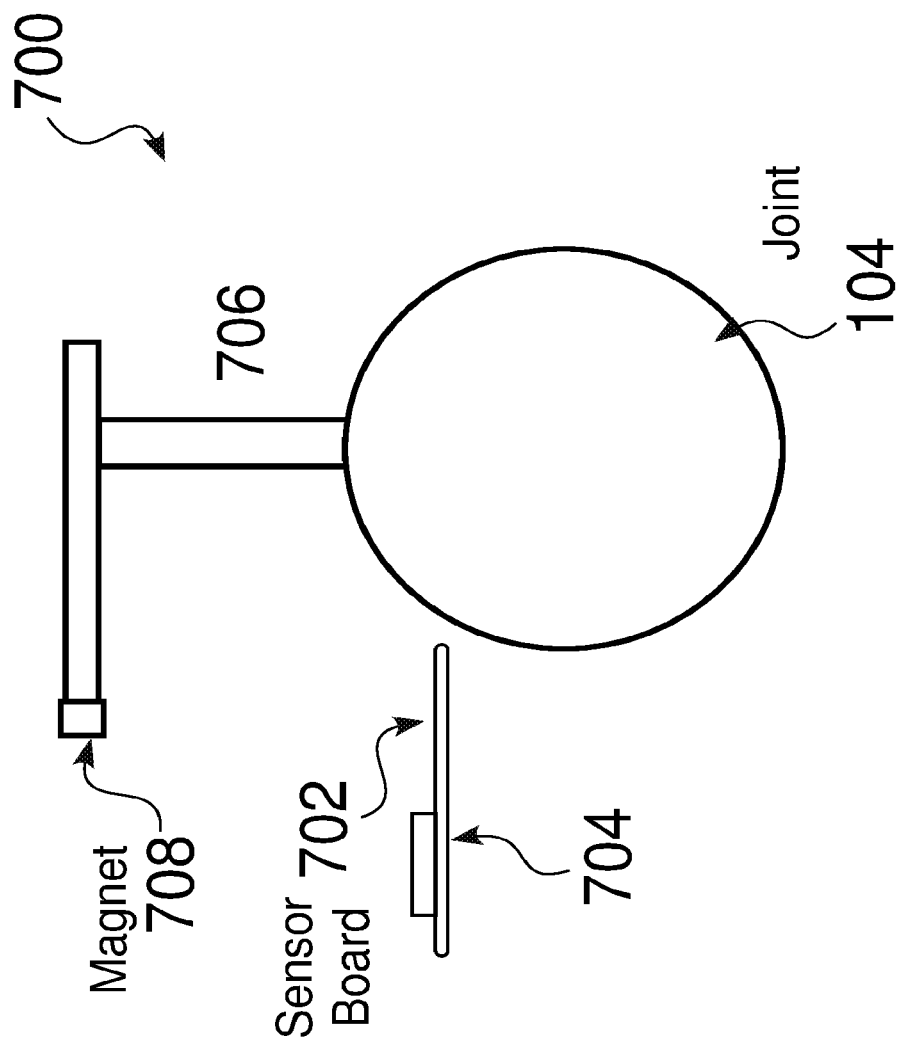
FIG. 11 is a schematic side view of an illustrative electronically adjustable joint.
Figure 12:
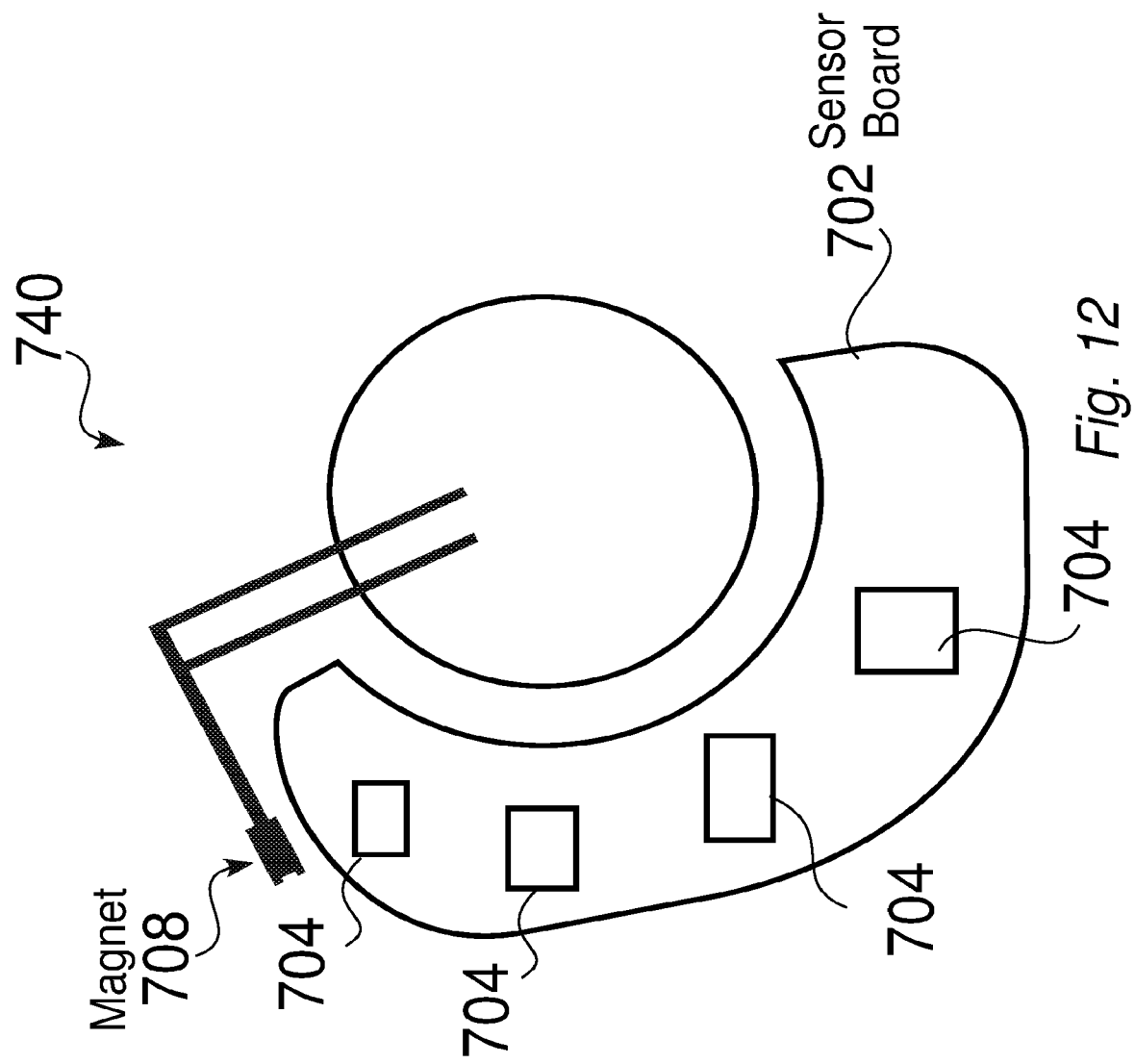
FIG. 12 is a plan view of an illustrative electronically adjustable joint.

FIG. 11 is a schematic side view 700 of an illustrative electronically adjustable joint 102. FIG. 12 is a plane view 740 of an illustrative electronically adjustable joint 102. The electronically adjustable joint 102 seen in FIG. 11 and FIG. 12 is configured to allow tracking of rotational movement 120 between joint components. For instance, the ball member 104 shown in FIG. 11 and FIG. 12 has associated therewith a magnet 708 corresponding thereto, such as fixedly connected 706, such that rotational movement 102 of the ball member 104 also results in movement of the magnet 108. As also seen in FIG. 11 and FIG. 12, a sensor board 702, having a plurality of sensors 704, is arranges in an sensors 704, is arranged in an illustrative joint 102, such as affixed with respect to a socket assembly 106. Rotational movement 120 of the magnet 708 with respect to the sensor board 702 is determined by the outputs of the plurality of sensors 704.

Figure 13:
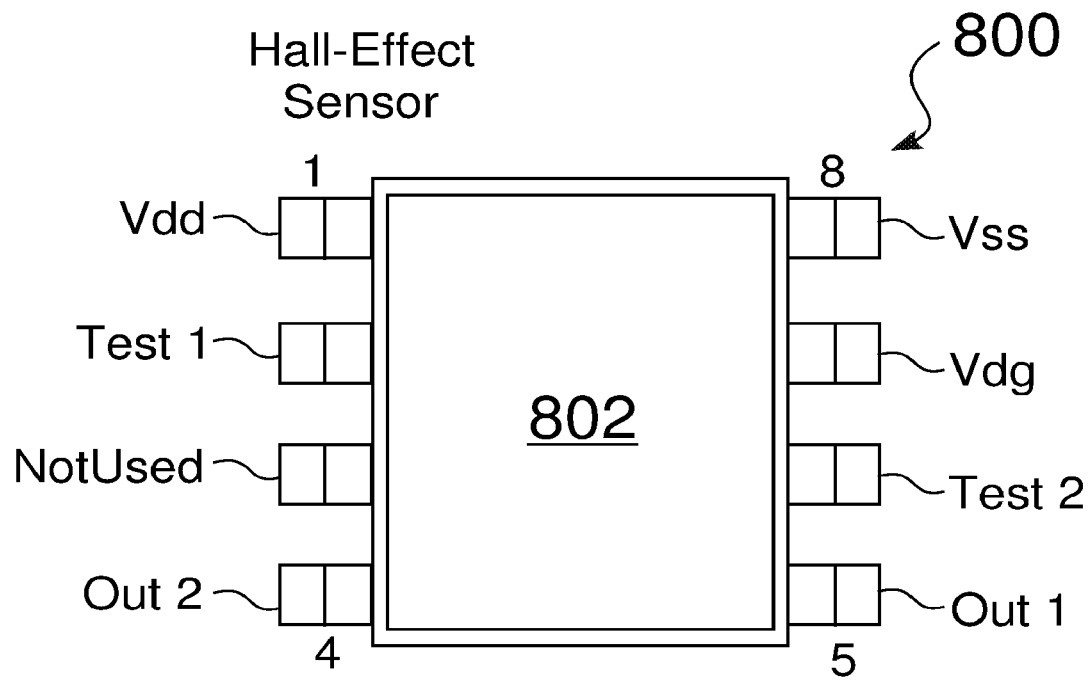
FIG. 13 is a schematic view of an illustrative Hall effect sensor for a sensor board of an electronically adjustable joint.
Figure 14:
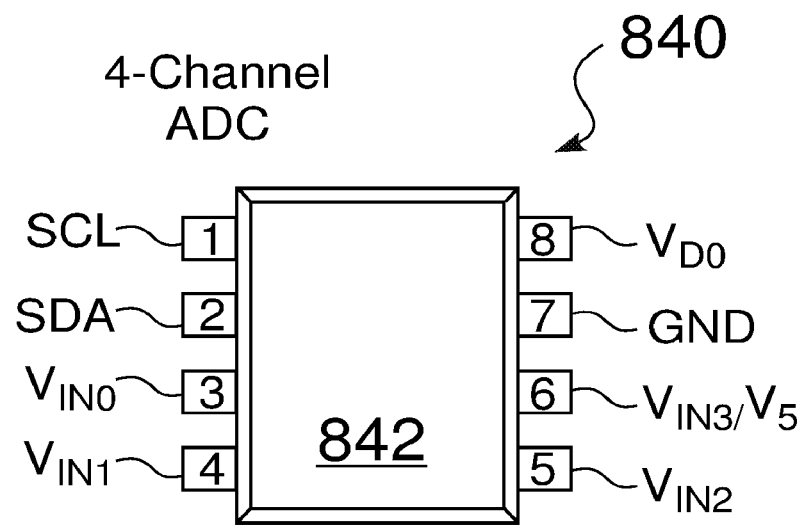
FIG. 14 is a schematic view of an illustrative 4-Channel analog-digital converter (ADC) for a sensor board of an electronically adjustable joint.

FIG. 13 is a schematic view 800 of a Hall effect sensor for an electronically adjustable joint. FIG. 14 is a schematic view of 900 a 4-Channel ADC for an electronically adjustable joint.

Figure 15:
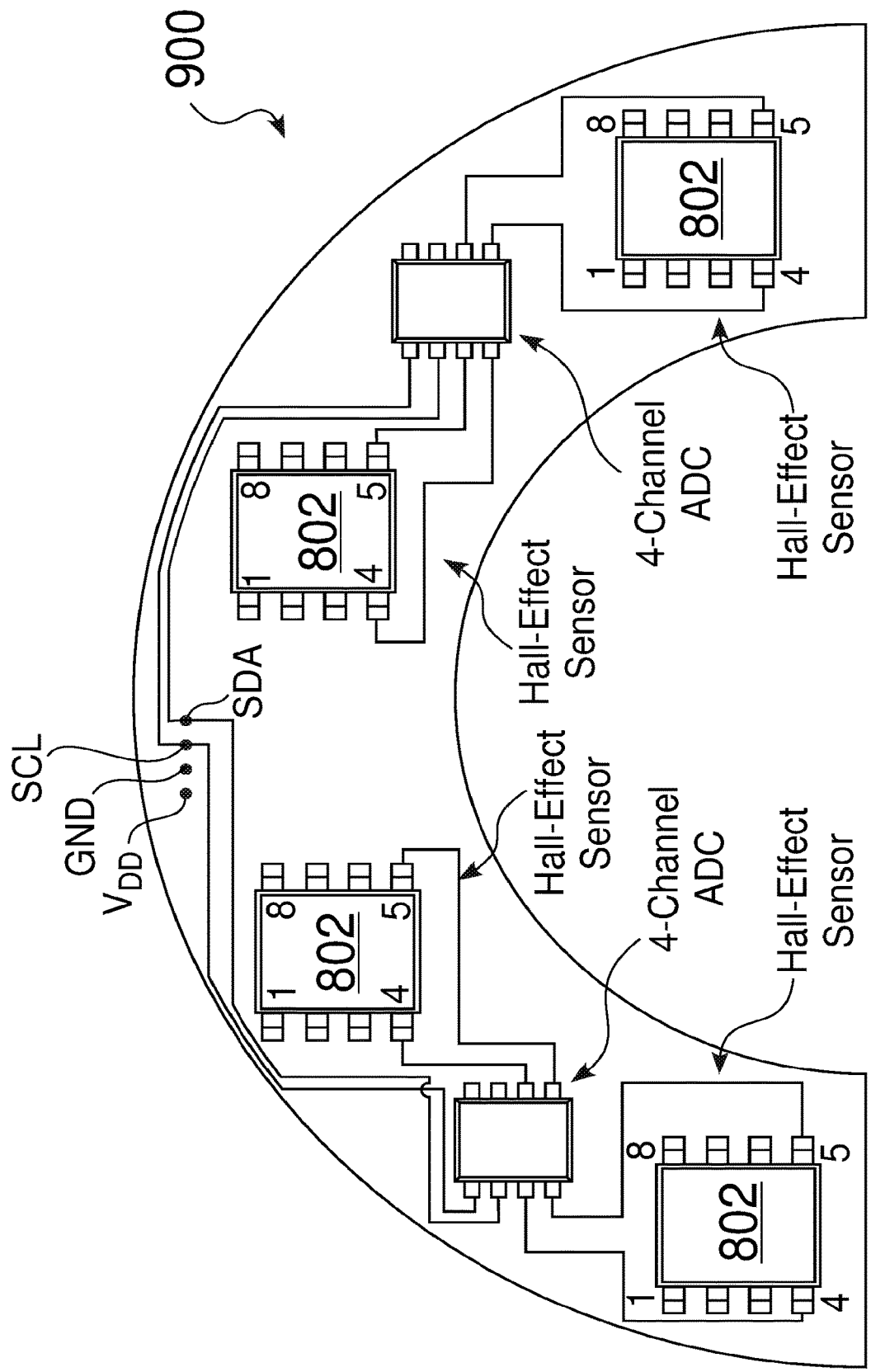
FIG. 15 is a schematic view of an illustrative sensor board that includes magnetometers and support circuitry for an electronically adjustable joint.

FIG. 15 is a schematic view 900 of a sensor board that includes magnetometers and support circuitry for an electronically adjustable joint.

Figure 16:
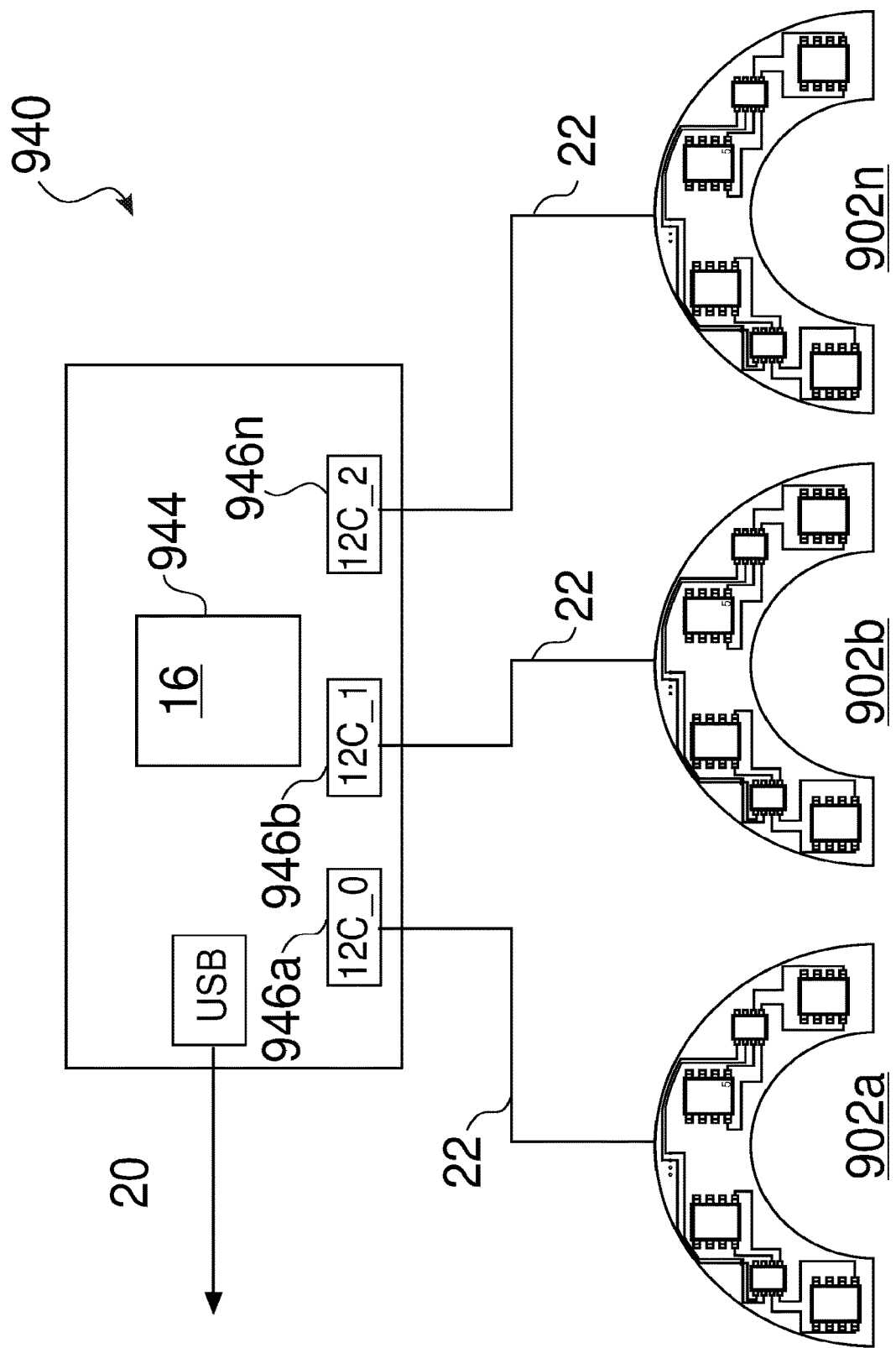
FIG. 16 schematic view of an interface between one or more sensor boards and a corresponding microcontroller for a plurality of electronically adjustable joints.

FIG. 16 is a schematic view 940 of an interface between one or more sensor boards for electronically adjustable joints and a corresponding microcontroller.

Figure 17:
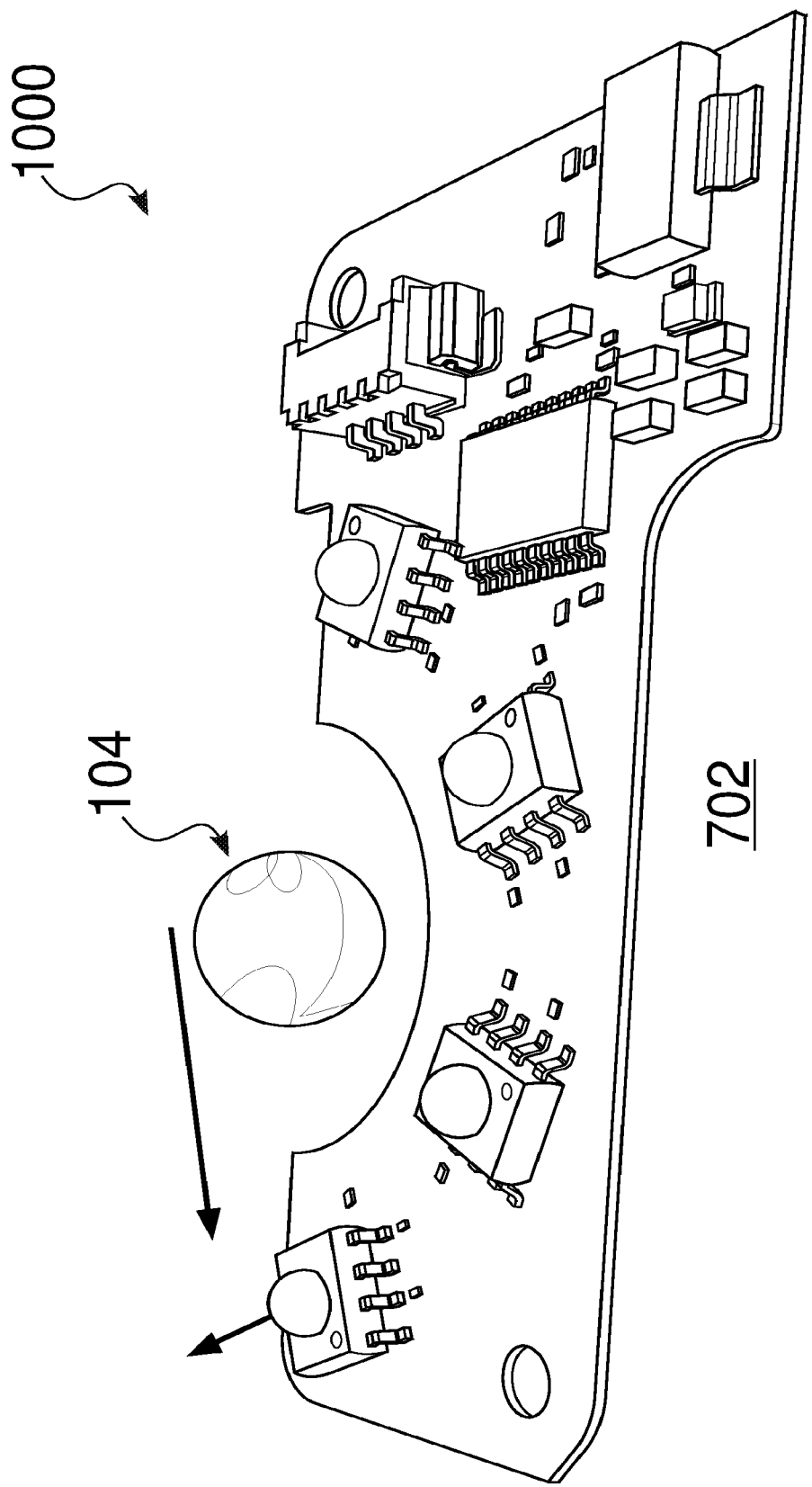
FIG. 17 is a detailed perspective view of a sensor board as schematically arranged with a ball assembly of an electronically adjustable joint

FIG. 17 is a detailed perspective view 1000 of a sensor board as arranged with respect to a ball assembly of an electronically adjustable joint.

Figure 18:
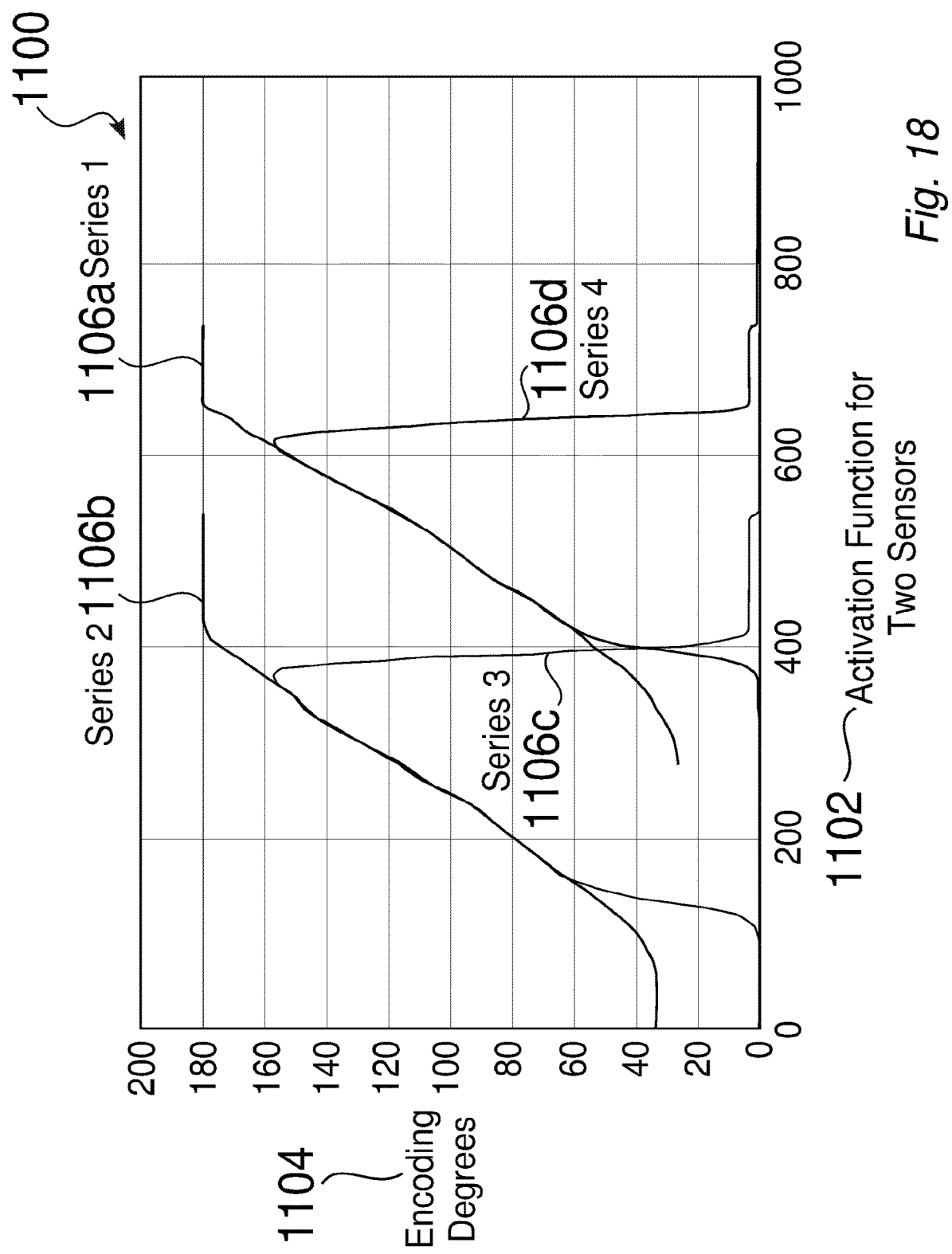
FIG. 18 is a graph that shows an activation function plotted for two sensors for a sensor board of an electronically adjustable joint.

FIG. 18 is a graph 1100 that shows an activation function plotted for two sensors. The Y-axis is encoding degrees.

FIG. 19 depicts the joint architecture 1200.

Figure 20:
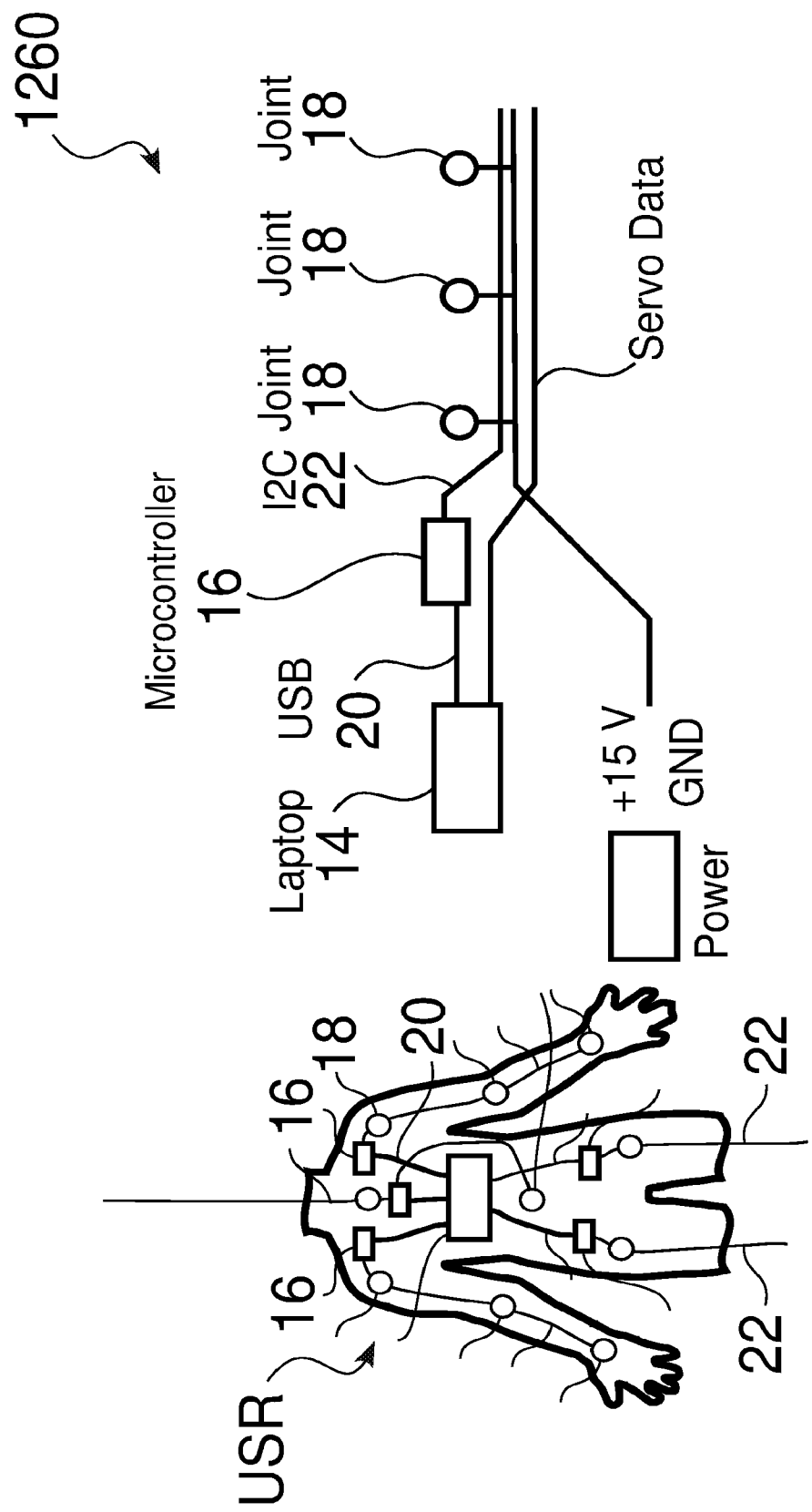
FIG. 20 is a simplified schematic view of a wiring harness as referenced to the conceptualized architecture seen in FIG. 1.

FIG. 20 is a function diagram 1260 of the wiring harness, drawing reference to the previously conceptualized architecture.

Figure 21:
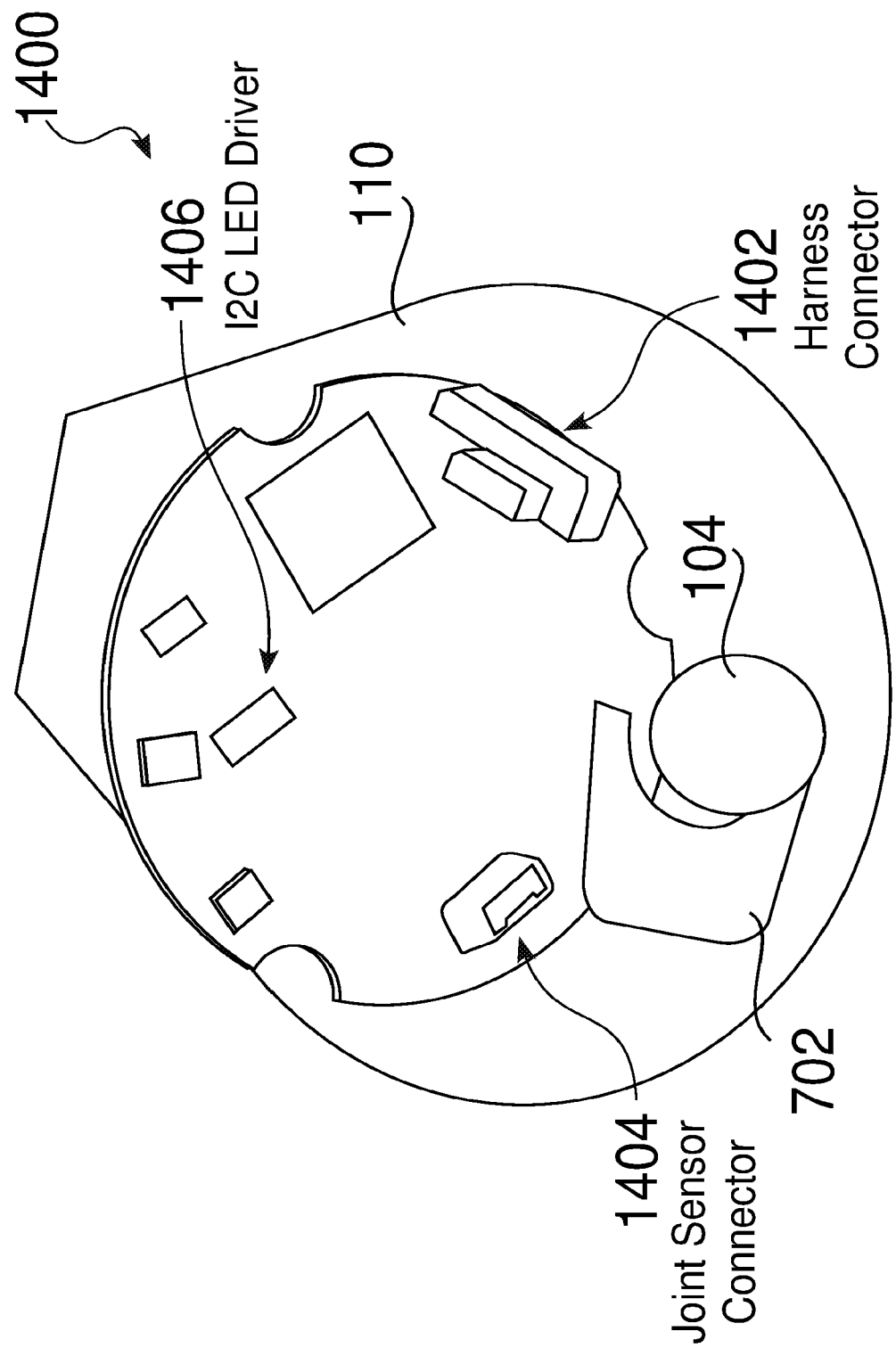
FIG. 21 depicts the relative placement of electronic boards for an illustrative sensor board.

FIG. 21 depicts the relative placement 1400 of the electronic boards for an illustrative electronically adjustable joint 102. For example, the sensor board 702 is arranged such that relative motion 120 of the ball assembly 104 and ball pivot arm 104 (FIG. 3) with respect to the socket pivot arm 110 is sensed through the sensor board 702. FIG. 21 also shows illustrative placement for a corresponding joint sensor connector 1404 and harness connector 1402.

Detailed Views of Joint Mechanism

Figure 22:
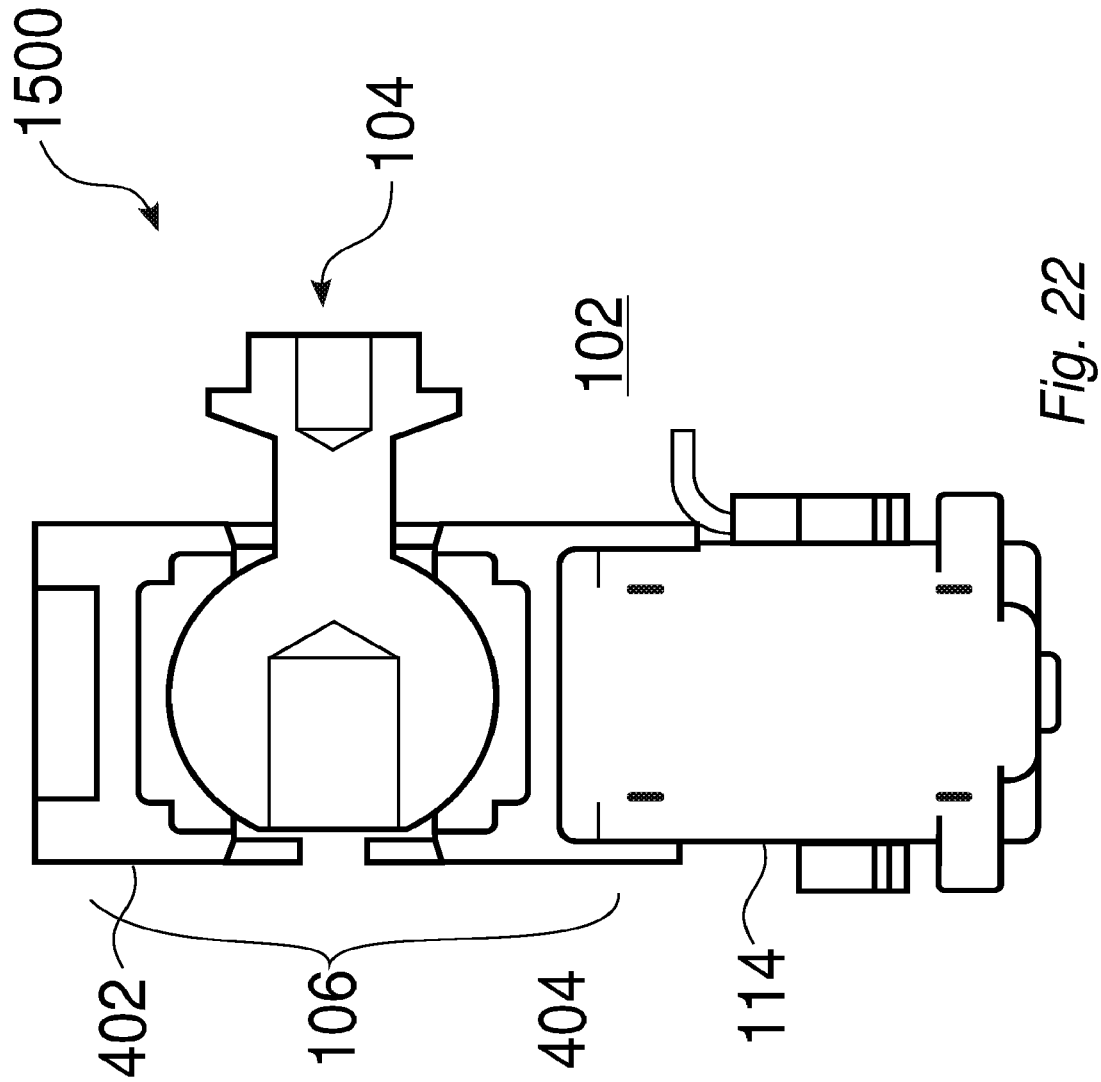
FIG. 22 is a partial cutaway end view of an illustrative electronically adjustable joint.
Figure 23:
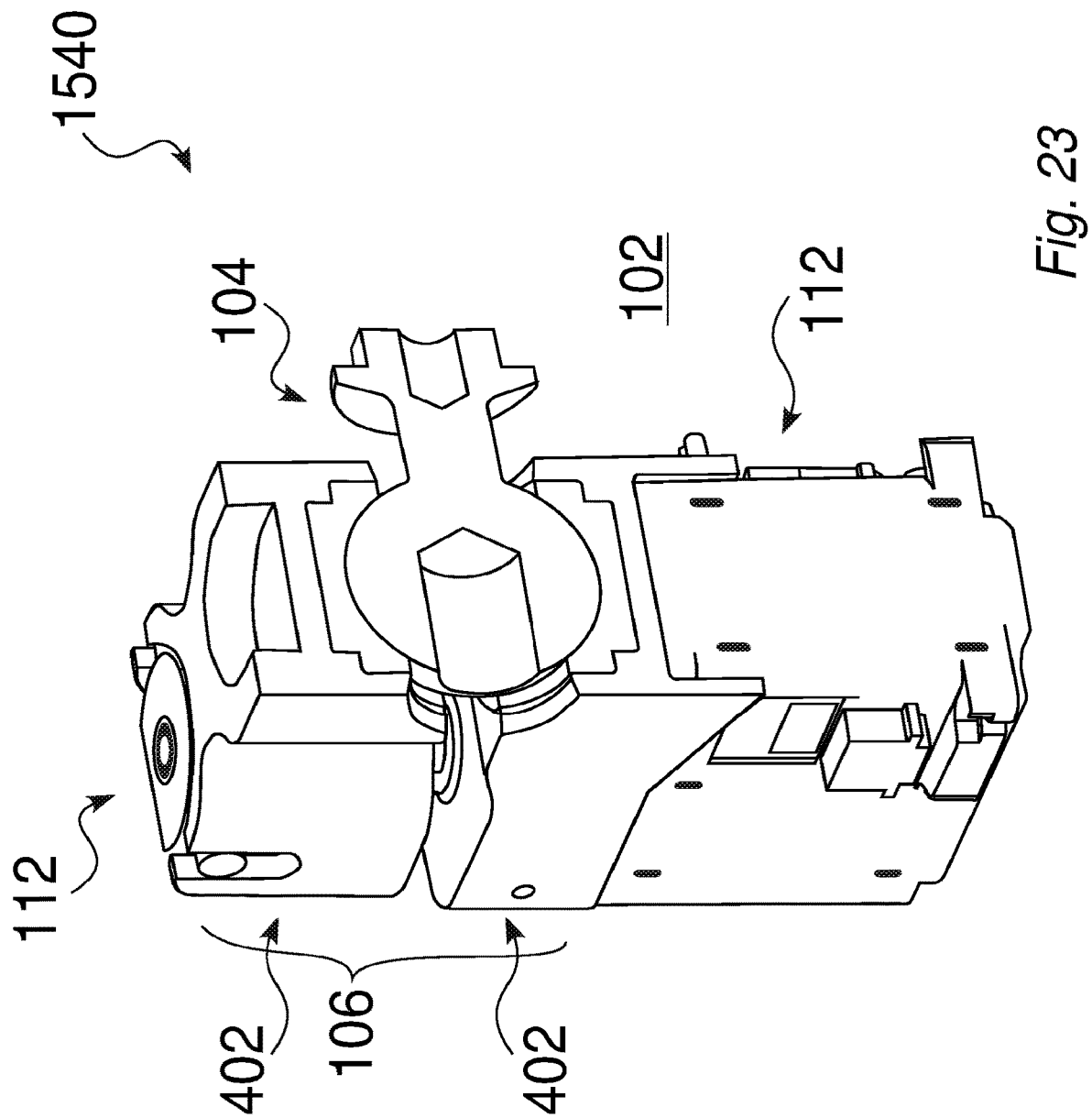
FIG. 23 is a partial cutaway perspective view of an illustrative electronically adjustable joint.
Figure 24:
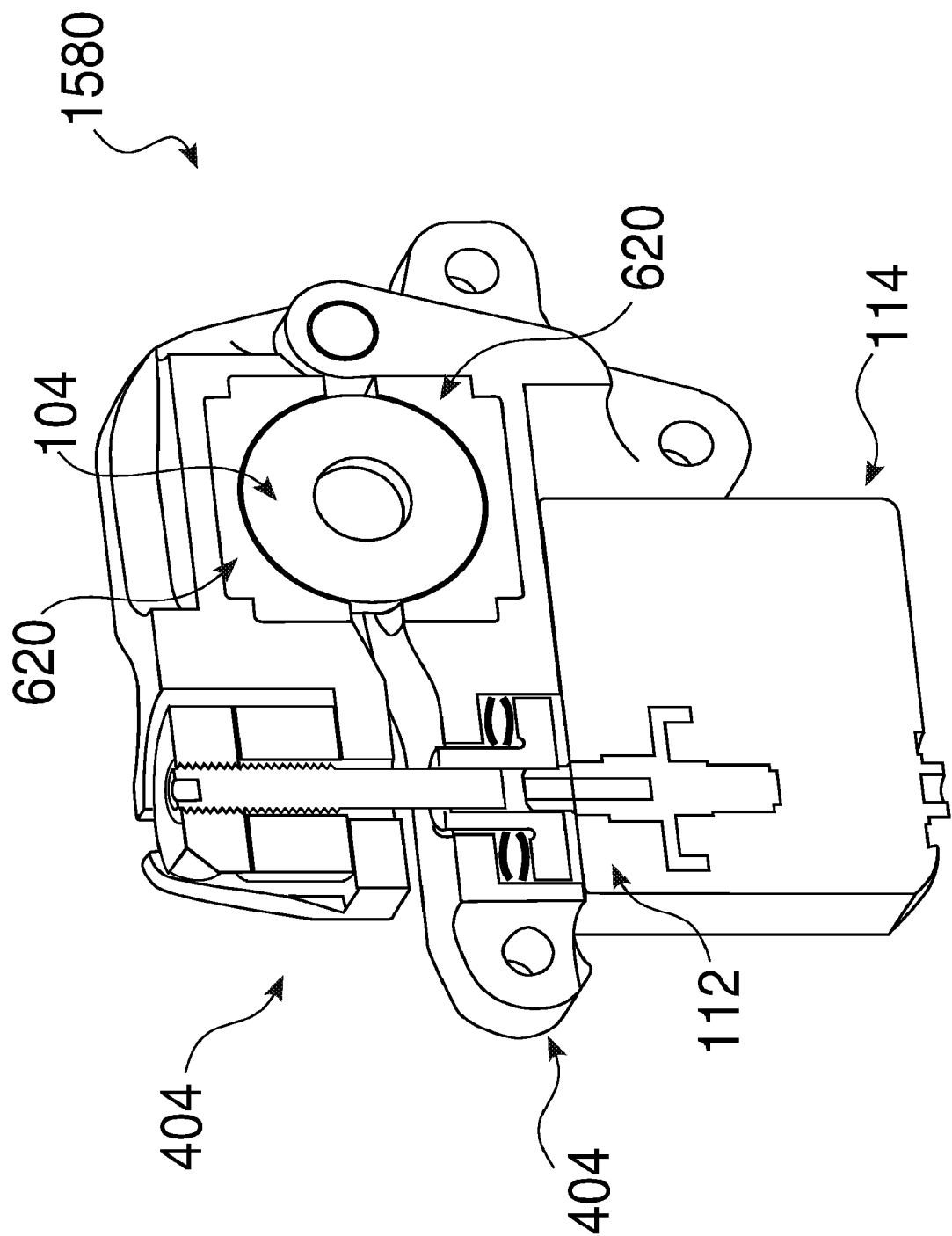
FIG. 24 is an alternate partial cutaway perspective view of an illustrative electronically adjustable joint.

FIG. 22 is a partial cutaway end view 1500 of an illustrative electronically adjustable joint 102. FIG. 23 is a partial cutaway perspective view 1540 of an illustrative electronically adjustable joint. FIG. 24 is an alternate partial cutaway perspective view 1580 of an illustrative electronically adjustable joint. FIG. 25 is partial cutaway side view 1600 of an illustrative electronically adjustable joint.

Joint Wiring Overview

In an illustrative embodiment, each joint on the suit 62 has a circuit board to provide a common interface to the suit harness. The suit harness provides power and communication to the servos, joint sensors, and joint lighting and can be in a daisy-chained configuration for each branch in the suit. The current power architecture is a star design with each circuit containing around three joints which each include a servo 114, a sensor board 702, and lighting.

In an illustrative embodiment each joint 102 connects to the harness and distributes the power and data to the joint component. Each joint 102 tees off the harness by a single connection. The harness also includes a spare data line for future expansion.

3-Axis Joint Sensing

Illustrative embodiments of the system are configured to determine 3-axis joint location. For instance, in some embodiments, an array of magnetometers 704 (4 are illustrated herein) provide spatial sensing of a 3-axis joint. The magnetometers 704 used in this illustrative embodiment have been interfaced and can provide a vector which points to the centroid of a nearby magnet 708. By positioning a magnet 708 on the end of an arm, e.g., a corresponding ball pivot arm 108, and by fixing the arm 108 to the ball 104 which makes up the joint, both the elevation and rotation information of the magnet 708 can be determined, using multiple magnetometers 704. FIG. 12 depicts the general arrangement.

The sensor board 702 contains the magnetometers 704, and support circuitry, and the magnet 708 can be fixed to the ball 104 via a shaft and/or cantilever. As the ball 104 rotates, the vectors from each magnetometer 704 can be used to identify the location of the magnet 708 in 30 space.

Sensor Board

In an illustrative embodiment, such as disclosed below, magnetometers can be arranged on a sensor board, which can be mounted around each joint:

ADC Interface

The 8-channel ADC is interfaced to the PC through a microcontroller (via 12C to the ADC). Each magnetometer has two outputs, an X and a Y. The channels are arranged such that they correspond to the magnetometer's location. A value of "6" is essentially zero volts, and a value of 4095 is 4.095V measured. Although the magnetometers can output higher than 4V, they are capped at 4.095V.

Joint Estimation

The position of the joint can be estimated from the readings of each magnetometer on the joint sensor board. These sensors output and x-y angle (two values each), which can be used to detect rotation and axis of the joint. In looking at the raw data, it appears that that mechanical structure sufficiently disrupts the field uniformity as seen from the sensors, so projecting a vector onto a spherical surface can be challenging. This is easier to understand if one considers that the magnet is not a point source and that the centroid calculation performed at any given sensor is dependent on the field lines at the sensor, which can be disturbed by the structure.

In an illustrative embodiment, to achieve a quick estimation of the joint sensor location, data was taken from the sensor interface in the form of a sweep around the sensor board with the arm. The sensor readings were captured and, although done by hand, the sweep was done at the most consistent rate as possible with the hand while constraining the joint rotational axis to a plane normal to the sensor array.

A machine learning approach can be used to process the data. Although a number of methods have been tried, an ensemble method (gradient boosting regressors) seemed to work best. Although multiple datasets were taken and tried, the best approach was to use a single dataset for a basic machine memorization. From this, a rough estimate of the joint location can be obtained, which is acceptable for servo control.

Challenges with Joint Estimation

One method found to continuously sense and track the angle of the joint is to use four discrete 2-axis magnetometers to calculate the position of the magnet on the arm of the joint. The goal is to continuously sense the magnet position.

However, it is challenging to keep track of the magnet as it passes through each sensor domain. For example, as it sweeps though the arc, a sensor can eventually lose track of the magnet as it moves over the other sensors. This produces a boundary condition that may not be captured in the angle calculation. The result is choppy joint-angle calculation as the joint moves through the sweep. Since the magnet is not a point source but has dimensions, it cannot be located exactly by mapping onto a sphere.

One option is to use machine learning to map magnetometer output against observed arm position. This has proven effective, except for boundary conditions where the magnet is transitioning between two sensors. It would be desirable to suppress outputs with low confidence where the sensor is just starting to sense the magnet, and again where the sensor is saturated at the maximum level. Thus, the boundary conditions would be smoothed out and the joint position resolved at any point in its motion.

To address the issue, sigmoid activation functions can be applied to calculate confidence levels which are then used as weights in a weighted average of each joint sensor output. The individual sensors are translated appropriately so that a map can be created between sensor outputs and output angle. By using this as an input to the learning algorithm, the location of the magnet in 30 space can be obtained. This is necessary for accurate avatar display.

Note that any and all of the embodiments described above can be combined with each other, except to the extent that it may be stated otherwise above or to the extent that any such embodiments might be mutually exclusive in function and/or structure.

Although the present invention has been described with reference to specific exemplary embodiments, it will be recognized that the invention is not limited to the embodiments described but can be practiced with modification and alteration within the spirit and scope of the appended claims. Accordingly, the specification and drawings are to be regarded in an illustrative sense rather than a restrictive sense.

What is claimed is:

1. A device comprising:
   a first joint mechanism, wherein a portion of the first joint mechanism includes a ball component;
   a second joint mechanism, wherein the second joint mechanism is configured with a plurality of members which together form an adjustable housing that adjustably houses the ball component;
   a third joint mechanism, wherein a first portion of the third joint mechanism is a magnetic element fixedly coupled to the housed ball component such that rotational movement of the ball component also results in movement of the magnet element, and a second portion of the third joint mechanism is fixedly coupled to at least one member of the second joint mechanism; and
   a fourth joint mechanism, wherein the fourth joint mechanism is operably coupled to the second joint mechanism via an adjustable joint screw element.

2. The device of claim 1, wherein a portion of the first joint element includes a fastening assembly coupled to the ball component via a shaft.

3. The device of claim 1, wherein the adjustable housing comprises at least two opposing members adjustably coupled to each other via a pivot connection.

4. The device of claim 3, wherein one of the at least two opposing members is adjustably coupled to the adjustable joint screw element.

5. The device of claim 4, wherein the fourth joint mechanism further comprises a brake pad or friction pad fixed to one or more inner housing surfaces of the one or more members of the second joint mechanism.

6. The device of claim 4, wherein the one opposing member adjustably coupled to the adjustable joint screw element is configured with a threaded engagement to the adjustable joint screw element.

7. The device of claim 3, wherein the fourth joint mechanism further comprises:
   a motor element; and
   a processor, wherein the processor is configured to receive a control signal and rotate the adjustable joint screw element, via the motor element, in response to the received control signal.

8. The device of claim 1, wherein the magnetic element coupled to the ball component is coupled via a lever arm.

9. The device of claim 8, wherein the lever arm is configured to support the magnetic element in triggerable proximity of one or more magnetic effect sensors of a sensor board assembly element.

10. The device of claim 1, wherein the second portion of the third joint mechanism comprises one or more magnetic effect sensors fixedly coupled to a circuit board assembly and in operable communication with the first portion of the third joint mechanism.

11. The device of claim 1, wherein the first joint mechanism is configured for rotation through two or more axis of rotation with respect to the second joint mechanism.

12. The device of claim 11, wherein the device is configured to simulate mechanical motion equivalent to any of a shoulder joint, an elbow joint, a hip joint, and a knee joint.

13. The device of claim 12, further comprising a mechanism for attachment to a user, wherein the device is aligned with a corresponding joint of the user, such that rotational friction can be adjusted at the device which resist rotational movement of the aligned corresponding user joint in one or more directions.

14. The device of claim 1, wherein the third joint mechanism comprises a mechanism for tracking movement of the ball component within the adjustable housing.

15. The device of claim 14, wherein the third joint mechanism includes a magnetic element in a fixed relation to the ball component, and a sensor assembly in fixed relation to the second joint mechanism, such that rotational movement of the ball component is determined based on voltage output levels of one or more magnetic effect sensor of the sensor assembly.

16. The device of claim 1, wherein the fourth joint mechanism comprises a mechanism for electronically adjusting friction around the ball component by driving a servo linked to the adjustable joint screw element, the adjustable joint screw element configured to tighten or loosen the adjustable housing with respect to the housed ball component.

* * * * *